United States Patent
Meissner et al.

(10) Patent No.: US 7,432,096 B2
(45) Date of Patent: Oct. 7, 2008

(54) GLUCOSE DEHYDROGENASE AND PRODUCTION THEREOF

(75) Inventors: Ruth Meissner, Leverkusen (DE); Walter Weichel, Odenthal (DE); Rainhard Koch, Kleinmachnow (DE); Irina Bachmatova, Vilnius (LT); Liucija Marcinkeviciene, Vilnius (LT); Rita Meskiene, Vilnius (LT); Rasa Semenaite, Vilnius (LT); Vida Casaite, Vilnius (LT); Rolandas Meskys, Vilnius (LT)

(73) Assignee: Bayer Technology Services GmbH, Leverkusen (DE)

(*) Notice: Subject to any disclaimer, the term of this patent is extended or adjusted under 35 U.S.C. 154(b) by 60 days.

(21) Appl. No.: 10/555,903

(22) PCT Filed: Apr. 27, 2004

(86) PCT No.: PCT/EP2004/004413

§ 371 (c)(1),
(2), (4) Date: Dec. 16, 2005

(87) PCT Pub. No.: WO2004/099399

PCT Pub. Date: Nov. 18, 2004

(65) Prior Publication Data

US 2006/0263838 A1 Nov. 23, 2006

(30) Foreign Application Priority Data

May 7, 2003 (DE) ............................... 103 20 259

(51) Int. Cl.
*C12N 9/02* (2006.01)
*C12N 1/12* (2006.01)
*C12Q 1/26* (2006.01)
*C12P 21/06* (2006.01)
*G01N 33/00* (2006.01)
*C07H 21/02* (2006.01)
*C07H 21/04* (2006.01)

(52) U.S. Cl. .................. 435/190; 435/25; 435/69.1; 435/252.3; 435/488; 435/14; 436/95; 536/23.1; 536/23.2

(58) Field of Classification Search .................. None
See application file for complete search history.

(56) References Cited

U.S. PATENT DOCUMENTS 7,037,698 B2 * 5/2006 Suzumura et al. ........... 435/190

FOREIGN PATENT DOCUMENTS

| EP | 1 167 519 A | 1/2002 |
|---|---|---|
| JP | 11 243949 | 12/1999 |
| JP | 2001 037483 | 2/2001 |
| JP | 2000 354495 | 4/2001 |
| JP | 2001 197888 | 7/2001 |
| WO | WO 02/34919 A | 5/2002 |
| WO | WO 02/34919 A1 | 5/2002 |

OTHER PUBLICATIONS

Sode et al., Increasing stability of the water soluble pyrroloquinoline quinone glucose dehydrogenase by a single amino acid replacement. Enzyme Microbiol. Tech., 2000, vol. 26: 491-496.*
Toyobo Co Ltd.; JP 11 243949 A—Patent Abstracts of Japan vol. 1999, No. 14, Dec. 22, 1999.
Hayade Koji, JP 2000 354495 A—Patent Abstracts of Japan, vol. 2000, No. 15, Dec. 26, 2000.
Laber B. et al.; "Vitamin B6 biosynthesis: formation of pyridoxine 5'-phosphate from 4-(phosphohydroxy)-1-threonine and 1-deoxy-d-xylulose-5-phosphate by PdxA and PdxJ protein"; Febs Letters, Elsevier Science Publishers, Amsterdam, NL; vol. 449, No. 1; Apr. 16, 1999 p. 45-48.
Takahashi Y. et al; "Construction and characterization of glucose enzyme sensor employing engineered water soluble PQQ glucose dehydrogenase with improved thermal stability"; Proceedings of the Voice I/O systems Applications Conference; vol. 68, No. 11, (2000); p. 907-911.
Sode K et al; "Increasing the thermal stability of the water-soluble pyrroloquinoline quinine glucose dehydrogenase by single amino acid replacement"; Enzyme and Microbial Technology, Stoneham, MA, US; vol. 26, No. 7; Apr. 2001; p. 491-496.
Hayade Koji; JP 2001 037483 A; Patent Abstracts of Japan, vol. 2000, No. 19, Jun. 5, 2001.
Hayade Koji; JP 2001 197888 A; Patent Abstracts of Japan, vol. 2000, No. 24, May 11, 2001.
Cleton-Jansen A-M et al; "Cloning, characterization and DNA sequencing of the gene encoding the MR 50000 quinoprotein glucose dehydrogenase from acinetobacter calcoaceticus"; Molecular and General Genetics, Springer Verlag, Berlin, Germany, vol. 217, No. 2/3; Jun. 1989; p. 430-436.
Laber B. et al; "Vitamin $B_6$ biosynthesis: formation of pyridoxine 5'-phosphate from 4-(phosphohydroxy)-L-threonine and 1-deoxy-D-xylulose-5-phosphate by PdxA and PdxJ protein"; FEBS Letters 449 (1999); Elsevier Science Publishers, Amsterdam NL ; pp. 45-48.
Takahashi Yuka, et al; "Construction and characterization of glucose enzyme sensor employing engineered water soluble PQQ glucose dehydrogenase with improved thermal stability"; Proceedings of the Voice I/O Systems Applications Conference, XX; No. 11 (2000); pp. 907-911; XP 009028017.
Sode Koji, et al; "Increasing the thermal stability of the water-soluble pyrroloquinoline quinine glucose dehydrogenase by single amino acid replacement"; Enzyme and Microbial Technology; Stoneham, MA, US; 26 (2000); pp. 491-496; XP 001155036.
Cleton-Jansen Anne-Marie, et al; "Cloning, characterization and DNA sequencing of the gene encoding the M, 50 000 quinoproteine glucose dehydrogenase from *Acinetobactr calcoaceticus*"; Molecular and General Genetics; Springer Verlag, Berlin, Germany (1989); vol. 217; pp. 430-436; XP 000990490.

* cited by examiner

*Primary Examiner*—Rebecca E. Prouty
*Assistant Examiner*—Ganapathirama Raghu
(74) *Attorney, Agent, or Firm*—Norris McLaughlin & Marcus PA

(57) ABSTRACT

The invention relates to novel PQQ-dependent soluble glucose dehydrogenases (sPQQGDH) from *Acinetobacter* and to a process for their preparation by overexpression in suitable microbial expression systems.

9 Claims, 3 Drawing Sheets

```
             430       440       450       460       470       480
          ----+---------+---------+---------+---------+---------+
          DDAVPMFKSNNRYRDVIASPDGNVLYVLITDTAGNVQKDDGSVINTLENPGSLIKFTYKAK.  LMD79.41
          ...I........E.T............S............H..............NG..  E28183 JCM6841
          .................................................R.....Q..  PT16
          ..........................S......................R.....Q..  KOZ62
          ..........................S......................R.....Q..  PTN69
          ..........................S......................R.....Q..  KOZ65
          ..........................S......................R.....Q..  KG106
          ..........................S......................R.....Q..  PTN26
          ..........................S......................R.....Q..  PT15
          ..........................S......................R.....Q..  KGN80
          ..........................S......................R.....Q..  KG140
          ..........................S......................R.....Q..  KGN34
          ..........................S......................R.....Q..  KGN25
          ..........................S......................R.....Q..  KGN100
```

FIG. 1E

SEQUENCE LISTING

<160> NUMBER OF SEQ ID NOS: 28

<210> SEQ ID NO 1
<211> LENGTH: 1437
<212> TYPE: DNA
<213> ORGANISM: Acinetobacter sp.

<400> SEQUENCE: 1

```
atgaataaac atttattggc taaaattgct ttattaagcg ctgttcagct agttacactc      60
tcagcatttg ctgatgttcc tctaactcca tctcaatttg ctaaagcgaa atcagagaac     120
tttgacaaga aagttattct atctaatcta aataagccgc atgctttgtt atggggacca     180
gataatcaaa tttggttaac tgagcgagca acaggtaaga ttctaagagt taatccagag     240
tcgggtagtg taaaaacagt ttttcaggta ccagagattg tcaatgatgc tgatgggcag     300
aatggtttat taggttttgc cttccatcct gattttaaaa ataatcctta tatctatatt     360
tcaggtacat ttaaaaatcc gaaatctaca gataaagaat taccgaacca aacgattatt     420
cgtcgttata cctataataa atcaacagat acgctcgaga agccagtcga tttattagca     480
ggattacctt catcaaaaga ccatcagtca ggtcgtcttg tcattgggcc agatcaaaag     540
atttattata cgattggtga ccaagggcgt aaccagcttg cttatttgtt cttgccaaat     600
caagcacaac atacgccaac tcaacaagaa ctgaatggta aagactatca cacctatatg     660
ggtaaagtac tacgcttaaa tcttgatgga agtattccaa aggataatcc aagtttttaac    720 ggggtggtta gccatattta tacacttgga catcgtaatc cgcagggctt agcattcact     780
ccaaatggta aattattgca gtctgaacaa ggcccaaact ctgacgatga aattaacctc     840
attgtcaaag gtggcaatta tggttggccg aatgtagcag gttataaaga tgatagtggc     900
tatgcttatg caaattattc agcagcagcc aataagtcaa ttaaggattt agctcaaaat     960
ggagtaaaag tagccgcagg ggtccctgtg acgaaagaat ctgaatggac tggtaaaaac    1020
tttgtcccac cattaaaaac tttatatacc gttcaagata cctacaacta taacgatcca    1080
acttgtggag agatgaccta catttgctgg ccaacagttg caccgtcatc tgcctatgtc    1140
tataagggcg gtaaaaaagc aattactggt tgggaaaata cattattggt tccatcttta    1200
```

```
aaacgtggtg tcattttccg tattaagtta gatccaactt atagcactac ttatgatgac   1260
gctgtaccga tgtttaagag caacaaccgt tatcgtgatg tgattgcaag tccagatggg   1320
aatgtcttat atgtattaac tgatactgcc ggaaatgtcc aaaaagatga tggctcagta   1380
acaaatacat tagaaaaccc aggatctctc attaagttca cctataaggc taagtaa     1437
```

<210> SEQ ID NO 2
<211> LENGTH: 478
<212> TYPE: PRT
<213> ORGANISM: Acinetobacter sp.

<400> SEQUENCE: 2

```
Met Asn Lys His Leu Leu Ala Lys Ile Ala Leu Leu Ser Ala Val Gln
1               5                   10                  15

Leu Val Thr Leu Ser Ala Phe Ala Asp Val Pro Leu Thr Pro Ser Gln
            20                  25                  30

Phe Ala Lys Ala Lys Ser Glu Asn Phe Asp Lys Lys Val Ile Leu Ser
        35                  40                  45

Asn Leu Asn Lys Pro His Ala Leu Leu Trp Gly Pro Asp Asn Gln Ile
    50                  55                  60

Trp Leu Thr Glu Arg Ala Thr Gly Lys Ile Leu Arg Val Asn Pro Glu
65                  70                  75                  80

Ser Gly Ser Val Lys Thr Val Phe Gln Val Pro Glu Ile Val Asn Asp
                85                  90                  95

Ala Asp Gly Gln Asn Gly Leu Leu Gly Phe Ala Phe His Pro Asp Phe
            100                 105                 110

Lys Asn Asn Pro Tyr Ile Tyr Ile Ser Gly Thr Phe Lys Asn Pro Lys
        115                 120                 125

Ser Thr Asp Lys Glu Leu Pro Asn Gln Thr Ile Ile Arg Arg Tyr Thr
    130                 135                 140

Tyr Asn Lys Ser Thr Asp Thr Leu Glu Lys Pro Val Asp Leu Leu Ala
145                 150                 155                 160

Gly Leu Pro Ser Ser Lys Asp His Gln Ser Gly Arg Leu Val Ile Gly
                165                 170                 175

Pro Asp Gln Lys Ile Tyr Tyr Thr Ile Gly Asp Gln Gly Arg Asn Gln
            180                 185                 190

Leu Ala Tyr Leu Phe Leu Pro Asn Gln Ala Gln His Thr Pro Thr Gln
        195                 200                 205

Gln Glu Leu Asn Gly Lys Asp Tyr His Thr Tyr Met Gly Lys Val Leu
    210                 215                 220

Arg Leu Asn Leu Asp Gly Ser Ile Pro Lys Asp Asn Pro Ser Phe Asn
225                 230                 235                 240

Gly Val Val Ser His Ile Tyr Thr Leu Gly His Arg Asn Pro Gln Gly
                245                 250                 255

Leu Ala Phe Thr Pro Asn Gly Lys Leu Leu Gln Ser Glu Gln Gly Pro
            260                 265                 270

Asn Ser Asp Asp Glu Ile Asn Leu Ile Val Lys Gly Gly Asn Tyr Gly
        275                 280                 285

Trp Pro Asn Val Ala Gly Tyr Lys Asp Asp Ser Gly Tyr Ala Tyr Ala
    290                 295                 300

Asn Tyr Ser Ala Ala Ala Asn Lys Ser Ile Lys Asp Leu Ala Gln Asn
305                 310                 315                 320

Gly Val Lys Val Ala Ala Gly Val Pro Val Thr Lys Glu Ser Glu Trp
                325                 330                 335
```

Thr Gly Lys Asn Phe Val Pro Pro Leu Lys Thr Leu Tyr Thr Val Gln
         340                 345                 350

Asp Thr Tyr Asn Tyr Asn Asp Pro Thr Cys Gly Glu Met Thr Tyr Ile
         355                 360                 365

Cys Trp Pro Thr Val Ala Pro Ser Ser Ala Tyr Val Tyr Lys Gly Gly
         370                 375                 380

Lys Lys Ala Ile Thr Gly Trp Glu Asn Thr Leu Leu Val Pro Ser Leu
385                 390                 395                 400

Lys Arg Gly Val Ile Phe Arg Ile Lys Leu Asp Pro Thr Tyr Ser Thr
                 405                 410                 415

Thr Tyr Asp Asp Ala Val Pro Met Phe Lys Ser Asn Asn Arg Tyr Arg
         420                 425                 430

Asp Val Ile Ala Ser Pro Asp Gly Asn Val Leu Tyr Val Leu Thr Asp
         435                 440                 445

Thr Ala Gly Asn Val Gln Lys Asp Asp Gly Ser Val Thr Asn Thr Leu
         450                 455                 460

Glu Asn Pro Gly Ser Leu Ile Lys Phe Thr Tyr Lys Ala Lys
465                 470                 475

<210> SEQ ID NO 3
<211> LENGTH: 1443
<212> TYPE: DNA
<213> ORGANISM: Acinetobacter sp.

<400> SEQUENCE: 3

| | | | | | | |
|---|---|---|---|---|---|---|
| atgaataaac | atttattagc | aaaaatcact | cttttaggtg | ctgcacaact | atttacgttt | 60 |
| catacggcat | ttgcagatat | acctctgaca | cctgctcagt | tcgcaaaagc | gaaaacagaa | 120 |
| aattttgata | aaaaagtgat | tctgtccaat | ttaaataaac | cacatgcttt | gttatggggg | 180 |
| ccagataatc | aaatttggtt | aaccgaacgt | gcaactggca | aaattttaag | agtaaatcct | 240 |
| gtatctggta | gcgcgaaaac | agtatttcag | gttcctgaaa | ttgtgagtga | tgctgatggg | 300 |
| caaaatggtt | tgttaggttt | tgcttttcat | cctgacttta | acataacccc | ttatatctat | 360 |
| atttcaggca | cttttaaaaa | tccaaaatct | acagataaag | agttacctaa | tcagacaatt | 420 |
| attcgtagat | atacctataa | taaaactaca | gatacatttg | aaaagcctat | tgatttgatt | 480 |
| gcaggtttac | cgtcatcaaa | agatcatcag | tctggtcgtc | tcgttattgg | tccagaccaa | 540 |
| aaaatctact | atacgattgg | tgaccaaggt | cgtaatcagt | tagcttatct | attcttatcg | 600 |
| aatcaggcac | agcatactcc | gactcagcaa | gagctcaata | gtaaagacta | ccatacatat | 660 |
| atgggtaaag | tattacgctt | aaatctggac | ggcagtatac | ctaaagacaa | cccaagcttt | 720 |
| aacggcgtag | tgagtcatat | ctacacttta | gggcaccgta | atccacaagg | tttagcattt | 780 |
| gccccaaatg | gaaagctttt | acaatctgag | caagggccaa | attctgatga | tgaaattaac | 840 |
| cttgtattaa | aaggtggtaa | ctatggctgg | ccaaatgtag | ctggttataa | agatgacagt | 900 |
| ggttatgcct | atgcaaacta | ttcggcagca | accataaat | cacaaattaa | agatttagct | 960 |
| caaaacggga | taaagtagc | aacaggtgtt | cctgtgacta | agagtctga | atggactggt | 1020 |
| aaaaactttg | tgccaccttt | gaaaacttta | tatacggtac | aagataccta | taactataat | 1080 |
| gaccctactt | gtggtgagat | ggcatatatt | tgctggccaa | cggttgcacc | gtcatcggca | 1140 |
| tatgtatata | cgggaggcaa | aaaagcgatt | ccagggtggg | aaaatacatt | attggtccca | 1200 |
| tctttaaaac | gtggggtgat | tttccgtatt | aaattggacc | cgacatatag | cacgactttg | 1260 |
| gatgatgcta | tcccaatgtt | taaagcaat | aaccgttatc | gtgatgtcat | cgctagtcca | 1320 |

-continued

```
gaaggtaata ccttatatgt gctgactgat acagcgggaa atgtacaaaa agatgatggt    1380
tcagtcactc atactttaga gaatcccggt tctctcatta aatttacata taacggtaag    1440
taa                                                                  1443
```

<210> SEQ ID NO 4
<211> LENGTH: 480
<212> TYPE: PRT
<213> ORGANISM: Acinetobacter sp.

<400> SEQUENCE: 4

```
Met Asn Lys His Leu Leu Ala Lys Ile Thr Leu Leu Gly Ala Ala Gln
 1               5                  10                  15

Leu Phe Thr Phe His Thr Ala Phe Ala Asp Ile Pro Leu Thr Pro Ala
            20                  25                  30

Gln Phe Ala Lys Ala Lys Thr Glu Asn Phe Asp Lys Lys Val Ile Leu
        35                  40                  45

Ser Asn Leu Asn Lys Pro His Ala Leu Leu Trp Gly Pro Asp Asn Gln
    50                  55                  60

Ile Trp Leu Thr Glu Arg Ala Thr Gly Lys Ile Leu Arg Val Asn Pro
65                  70                  75                  80

Val Ser Gly Ser Ala Lys Thr Val Phe Gln Val Pro Glu Ile Val Ser
                85                  90                  95

Asp Ala Asp Gly Gln Asn Gly Leu Leu Gly Phe Ala Phe His Pro Asp
            100                 105                 110

Phe Lys His Asn Pro Tyr Ile Tyr Ile Ser Gly Thr Phe Lys Asn Pro
        115                 120                 125

Lys Ser Thr Asp Lys Glu Leu Pro Asn Gln Thr Ile Ile Arg Arg Tyr
    130                 135                 140

Thr Tyr Asn Lys Thr Thr Asp Thr Phe Glu Lys Pro Ile Asp Leu Ile
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
            180                 185                 190

Gln Leu Ala Tyr Leu Phe Leu Ser Asn Gln Ala Gln His Thr Pro Thr
        195                 200                 205

Gln Gln Glu Leu Asn Ser Lys Asp Tyr His Thr Tyr Met Gly Lys Val
    210                 215                 220

Leu Arg Leu Asn Leu Asp Gly Ser Ile Pro Lys Asp Asn Pro Ser Phe
225                 230                 235                 240

Asn Gly Val Val Ser His Ile Tyr Thr Leu Gly His Arg Asn Pro Gln
                245                 250                 255

Gly Leu Ala Phe Ala Pro Asn Gly Lys Leu Leu Gln Ser Glu Gln Gly
            260                 265                 270

Pro Asn Ser Asp Asp Glu Ile Asn Leu Val Leu Lys Gly Gly Asn Tyr
        275                 280                 285

Gly Trp Pro Asn Val Ala Gly Tyr Lys Asp Asp Ser Gly Tyr Ala Tyr
    290                 295                 300

Ala Asn Tyr Ser Ala Ala Thr Asn Lys Ser Gln Ile Lys Asp Leu Ala
305                 310                 315                 320

Gln Asn Gly Ile Lys Val Ala Thr Gly Val Pro Val Thr Lys Glu Ser
                325                 330                 335

Glu Trp Thr Gly Lys Asn Phe Val Pro Pro Leu Lys Thr Leu Tyr Thr
```

```
              340             345             350
Val Gln Asp Thr Tyr Asn Tyr Asn Asp Pro Thr Cys Gly Glu Met Ala
            355                 360                 365
Tyr Ile Cys Trp Pro Thr Val Ala Pro Ser Ser Ala Tyr Val Tyr Thr
        370                 375                 380
Gly Gly Lys Lys Ala Ile Pro Gly Trp Glu Asn Thr Leu Leu Val Pro
385                 390                 395                 400
Ser Leu Lys Arg Gly Val Ile Phe Arg Ile Lys Leu Asp Pro Thr Tyr
                405                 410                 415
Ser Thr Thr Leu Asp Asp Ala Ile Pro Met Phe Lys Ser Asn Asn Arg
            420                 425                 430
Tyr Arg Asp Val Ile Ala Ser Pro Glu Gly Asn Thr Leu Tyr Val Leu
        435                 440                 445
Thr Asp Thr Ala Gly Asn Val Gln Lys Asp Asp Gly Ser Val Thr His
    450                 455                 460
Thr Leu Glu Asn Pro Gly Ser Leu Ile Lys Phe Thr Tyr Asn Gly Lys
465                 470                 475                 480

<210> SEQ ID NO 5
<211> LENGTH: 1443
<212> TYPE: DNA
<213> ORGANISM: Acinetobacter sp.

<400> SEQUENCE: 5
atgaataaac atttattggc taaaattact ttattaggtg ctgctcagct acttacgctc      60
aattcagcat tgctgatgt ccctcttact ccatctcaat tgctaaagc gaaaacagaa      120
agctttgata agaaagttct tctatctaat ttaaataagc acatgctttt gttgtggggg     180
cctgataatc aaatttggtt aacggagcgg gcaacaggta agattctaag agtgaatcca     240
gagtcgggca gtgtgaaaac agttttcag gttcctgaga ttgtaaatga tgctgatgga     300
caaaacggtt tattaggttt tgcttttcat cctgacttta acataatcc ttatatctat     360
gtttcaggta catttaaaaa tccgaaatct acagataaag aattaccgaa tcaaactatt     420
attcgtcgat ataccctaaa caaagcaaca gatactcttg agaaaccagt agatttatta     480
gcaggattac cttcatcgaa agaccatcag tcgggtcgcc ttgttattgg tccagaccaa     540
aagatttact atacgattgg tgatcaggga cgtaaccagc tggcttattt attcttacca     600
aatcaagcac agcatacgcc gactcaacag gaactgagcg gcaaagacta tcatacttat     660
atgggtaaag tattcgcctt aaatctggat ggaagtattc caaagataa tccaagcttt     720
aacggtgtaa ttagccatat tatacgctc ggtcatcgta acccacaggg cttggcattt     780
actccaaatg gtaaactgtt gcaatctgaa caaggtccaa actctgatga tgaaattaat     840
ctcattgtta aggtggtaa ctatggctgg ccaaatgtag ctggttataa agatgacagt     900
ggttatgcct atgcaaatta ttcggcagca accaataagt cacaaattaa agatttaggg     960
caaaatggag taaaagtagc ggcaggtgta cctgtgatga agagtctga atggagtggt    1020
aaaaactttg taccgccgtt aaaaacttta tataccgtcc aagatacctt aactataat    1080
gacccaactt gtggggatat gacctacatt tgctggccaa cagttgcgcc atcatctgct    1140
tatgtctata aggggggcaa aaaagcaatt tctggttggg aaaatacatt attggttcca    1200
tctttaaagc gtggtgttat tttccgtatt aagttagatc caacttacag tgctacttat    1260
gatgatgctg taccgatgtt taagagcaat aaccgttatc gtgacgtgat tgcaagtcca    1320
gatgggaatg ttttatatgt attgactgat acttccggaa atgtccaaaa ggatgatggc    1380
```

```
tctgtaacga atacattaga aaatccagga tctctgatta gatttacata taaagctcag    1440
taa                                                                 1443

<210> SEQ ID NO 6
<211> LENGTH: 480
<212> TYPE: PRT
<213> ORGANISM: Acinetobacter sp.

<400> SEQUENCE: 6

Met Asn Lys His Leu Leu Ala Lys Ile Thr Leu Leu Gly Ala Ala Gln
1               5                   10                  15

Leu Leu Thr Leu Asn Ser Ala Phe Ala Asp Val Pro Leu Thr Pro Ser
            20                  25                  30

Gln Phe Ala Lys Ala Lys Thr Glu Ser Phe Asp Lys Lys Val Leu Leu
        35                  40                  45

Ser Asn Leu Asn Lys Pro His Ala Leu Leu Trp Gly Pro Asp Asn Gln
    50                  55                  60

Ile Trp Leu Thr Glu Arg Ala Thr Gly Lys Ile Leu Arg Val Asn Pro
65                  70                  75                  80

Glu Ser Gly Ser Val Lys Thr Val Phe Gln Val Pro Glu Ile Val Asn
                85                  90                  95

Asp Ala Asp Gly Gln Asn Gly Leu Leu Gly Phe Ala Phe His Pro Asp
            100                 105                 110

Phe Lys His Asn Pro Tyr Ile Tyr Val Ser Gly Thr Phe Lys Asn Pro
        115                 120                 125

Lys Ser Thr Asp Lys Glu Leu Pro Asn Gln Thr Ile Ile Arg Arg Tyr
    130                 135                 140

Thr Tyr Asn Lys Ala Thr Asp Thr Leu Glu Lys Pro Val Asp Leu Leu
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
            180                 185                 190

Gln Leu Ala Tyr Leu Phe Leu Pro Asn Gln Ala Gln His Thr Pro Thr
        195                 200                 205

Gln Gln Glu Leu Ser Gly Lys Asp Tyr His Thr Tyr Met Gly Lys Val
    210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
                245                 250                 255

Gly Leu Ala Phe Thr Pro Asn Gly Lys Leu Leu Gln Ser Glu Gln Gly
            260                 265                 270

Pro Asn Ser Asp Asp Glu Ile Asn Leu Ile Val Lys Gly Gly Asn Tyr
        275                 280                 285

Gly Trp Pro Asn Val Ala Gly Tyr Lys Asp Asp Ser Gly Tyr Ala Tyr
    290                 295                 300

Ala Asn Tyr Ser Ala Ala Thr Asn Lys Ser Gln Ile Lys Asp Leu Gly
305                 310                 315                 320

Gln Asn Gly Val Lys Val Ala Ala Gly Val Pro Val Met Lys Glu Ser
                325                 330                 335

Glu Trp Ser Gly Lys Asn Phe Val Pro Pro Leu Lys Thr Leu Tyr Thr
            340                 345                 350
```

| | | | | | | | | | | | |
|---|---|---|---|---|---|---|---|---|---|---|---|
|Val|Gln|Asp|Thr|Tyr|Asn|Tyr|Asn|Asp|Pro|Thr|Cys|Gly|Asp|Met|Thr|
| | |355| | | |360| | | |365| | | | | |

Val Gln Asp Thr Tyr Asn Tyr Asn Asp Pro Thr Cys Gly Asp Met Thr
            355                 360                 365

Tyr Ile Cys Trp Pro Thr Val Ala Pro Ser Ser Ala Tyr Val Tyr Lys
        370                 375                 380

Gly Gly Lys Lys Ala Ile Ser Gly Trp Glu Asn Thr Leu Leu Val Pro
385                 390                 395                 400

Ser Leu Lys Arg Gly Val Ile Phe Arg Ile Lys Leu Asp Pro Thr Tyr
                405                 410                 415

Ser Ala Thr Tyr Asp Asp Ala Val Pro Met Phe Lys Ser Asn Asn Arg
                420                 425                 430

Tyr Arg Asp Val Ile Ala Ser Pro Asp Gly Asn Val Leu Tyr Val Leu
                435                 440                 445

Thr Asp Thr Ser Gly Asn Val Gln Lys Asp Asp Gly Ser Val Thr Asn
            450                 455                 460

Thr Leu Glu Asn Pro Gly Ser Leu Ile Arg Phe Thr Tyr Lys Ala Gln
465                 470                 475                 480

<210> SEQ ID NO 7
<211> LENGTH: 1443
<212> TYPE: DNA
<213> ORGANISM: Acinetobacter sp.

<400> SEQUENCE: 7

```
atgaataaac atttattggc taaaattact ttattaggtg ctgctcagct acttacgctc      60
aattcagcat ttgctgatgt ccctcttaca ccatctcaat ttgctaaagc gaaaacagaa     120
agctttgata agaaagttct tctatctaat ttaaataagc cacatgcttt gttgtgggga     180
cctgataatc aaatttggtt aacggagcgg gcaacaggta agattctaag agttaatcca     240
gagtcgggca gtgtaaaaac agttttttcag gttcctgaga ttgtaaatga tgctgatgga     300
caaaacggtt tattgggttt tgcctttcat cctgactta aaaataatcc ttatatctat      360
gtttcaggta catttaaaaa tccgaatctc acagataaag aattaccgaa tcaaactatt     420
atccgtcgat atacctataa caaggcaaca gatacccttg agaaaccagt agatttattg     480
gcaggattac cttcatcgaa agaccatcag tcgggtcgtc ttgtgattgg tccagaccaa     540
aagatttact atacgattgg tgatcaggga cgtaaccagc tggcttattt attcttacca     600
aatcaagcac agcatacgcc gactcaacag gaactgagcg gcaaagacta tcatacctat     660
atgggtaaag tattgcgctt aaatctggat ggaagtattc caaagagtaa tccaagctt t    720 aacggtgtaa ttagccatat ttatacgctc ggtcatcgta acccacaggg cttggcattt     780
actccaaatg gtaaactgtt gcaatctgaa cagggtccaa actctgatga tgaaattaac     840
ctcattgtca aaggtggtaa ctatggctgg ccaaatgtag cgggttataa agatgatagt     900
ggttatgcct atgcaaatta ttcggcagca agcaataaag cacaaattaa agatttagga     960
caaaatggtt aaaagtggc ggcagtgtta cctgtgatga aagagtctga atggactggt    1020
aaaaactttg taccgccgtt aaaaacttta tataccgtcc aagataccta aactataat     1080 gacccaactt gtggggatat gacctacatt tgctggccaa cggttgcgcc gtcatctgct    1140
tatgtctata agggaggcaa aaaagcaatt tctggttggg aaaatacatt attggttcca    1200
tctttaaagc gcggtgttat tttccgtatt aagctagatc caacttacag tactacttat    1260
gatgatgctg tgccgatgtt taagagcaac aatcgttatc gtgacgtgat tgcaagtcca    1320
gatgggaatg ttttatatgt attgactgat acttccggaa atgtccaaaa agatgatggt    1380
tctgtaacga atacattaga aaacccagga tctctgatta gatttacata taaagctcag    1440
```

```
                                                                       taa         1443
```

<210> SEQ ID NO 8
<211> LENGTH: 480
<212> TYPE: PRT
<213> ORGANISM: Acinetobacter sp.

<400> SEQUENCE: 8

```
Met Asn Lys His Leu Leu Ala Lys Ile Thr Leu Leu Gly Ala Ala Gln
1               5                   10                  15

Leu Leu Thr Leu Asn Ser Ala Phe Ala Asp Val Pro Leu Thr Pro Ser
            20                  25                  30

Gln Phe Ala Lys Ala Lys Thr Glu Ser Phe Asp Lys Lys Val Leu Leu
        35                  40                  45

Ser Asn Leu Asn Lys Pro His Ala Leu Leu Trp Gly Pro Asp Asn Gln
    50                  55                  60

Ile Trp Leu Thr Glu Arg Ala Thr Gly Lys Ile Leu Arg Val Asn Pro
65                  70                  75                  80

Glu Ser Gly Ser Val Lys Thr Val Phe Gln Val Pro Glu Ile Val Asn
                85                  90                  95

Asp Ala Asp Gly Gln Asn Gly Leu Leu Gly Phe Ala Phe His Pro Asp
            100                 105                 110

Phe Lys Asn Asn Pro Tyr Ile Tyr Val Ser Gly Thr Phe Lys Asn Pro
        115                 120                 125

Lys Ser Thr Asp Lys Glu Leu Pro Asn Gln Thr Ile Ile Arg Arg Tyr
    130                 135                 140

Thr Tyr Asn Lys Ala Thr Asp Thr Leu Glu Lys Pro Val Asp Leu Leu
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
            180                 185                 190

Gln Leu Ala Tyr Leu Phe Leu Pro Asn Gln Ala Gln His Thr Pro Thr
        195                 200                 205

Gln Gln Glu Leu Ser Gly Lys Asp Tyr His Thr Tyr Met Gly Lys Val
    210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
                245                 250                 255

Gly Leu Ala Phe Thr Pro Asn Gly Lys Leu Leu Gln Ser Glu Gln Gly
            260                 265                 270

Pro Asn Ser Asp Asp Glu Ile Asn Leu Ile Val Lys Gly Gly Asn Tyr
        275                 280                 285

Gly Trp Pro Asn Val Ala Gly Tyr Lys Asp Asp Ser Gly Tyr Ala Tyr
    290                 295                 300

Ala Asn Tyr Ser Ala Ala Ser Asn Lys Ala Gln Ile Lys Asp Leu Gly
305                 310                 315                 320

Gln Asn Gly Leu Lys Val Ala Ala Gly Val Pro Val Met Lys Glu Ser
                325                 330                 335

Glu Trp Thr Gly Lys Asn Phe Val Pro Pro Leu Lys Thr Leu Tyr Thr
            340                 345                 350

Val Gln Asp Thr Tyr Asn Tyr Asn Asp Pro Thr Cys Gly Asp Met Thr
        355                 360                 365
```

```
Tyr Ile Cys Trp Pro Thr Val Ala Pro Ser Ser Ala Tyr Val Tyr Lys
    370                 375                 380

Gly Gly Lys Lys Ala Ile Ser Gly Trp Glu Asn Thr Leu Leu Val Pro
385                 390                 395                 400

Ser Leu Lys Arg Gly Val Ile Phe Arg Ile Lys Leu Asp Pro Thr Tyr
                405                 410                 415

Ser Thr Tyr Asp Asp Ala Val Pro Met Phe Lys Ser Asn Asn Arg
            420                 425                 430

Tyr Arg Asp Val Ile Ala Ser Pro Asp Gly Asn Val Leu Tyr Val Leu
                435                 440                 445

Thr Asp Thr Ser Gly Asn Val Gln Lys Asp Asp Gly Ser Val Thr Asn
    450                 455                 460

Thr Leu Glu Asn Pro Gly Ser Leu Ile Arg Phe Thr Tyr Lys Ala Gln
465                 470                 475                 480
```

<210> SEQ ID NO 9
<211> LENGTH: 1443
<212> TYPE: DNA
<213> ORGANISM: Acinetobacter sp.

<400> SEQUENCE: 9

```
atgaataaac atttattggc taaaattact ttattaggtg ctgctcagct acttacactc     60
aattcagcat tgctgatgt ccctcttact ccatctcaat tgctaaagc gaaaacagaa      120
agctttgata agaaagttct ctatctcaat ttaaataagc cgcatgcttt gttgtgggga    180
cctgataatc aaatttggtt aacagagcgg gcaacaggta agattctaag agttaaccct    240
gaatcaggca gtgtaaaaac agttttcag gttcctgaga ttgtaaatga tgctgatgga    300
caaaacgggt tattgggttt tgcctttcat cctgacttta aaaataatcc ttatatctat    360
gtttcaggta catttaaaaa tccgaaatct acagataaag aattaccgaa tcaaactatt    420
atccgtcgat ataccctataa caaagcaaca gatactcttg agaaaccagt agatttatta   480
gcaggattac cttcatcgaa agaccatcag tcgggtcgcc ttgtgattgg tccagaccaa    540
aaaatttact atacgattgg tgatcagggg cgtaaccagc ttgcttattt attcttacca    600
aatcaggcac aacatacgcc gactcaacag gaactgagcg gcaaagacta tcatacctat    660
atgggtaaag tattacgctt aaatctggat ggaagtattc caaaagataa tccaagcttt    720
aacggtgtaa ttagccatat ttatacgctc ggtcatcgta acccacaggg cttggcattt    780
actccaaatg gtaaactgtt gcaatctgaa cagggtccaa actctgatga tgaaattaac    840
ctcattgtta aggtggtaa ctatggctgg ccaaatgcgg cgggttataa agatgacagt    900
ggttatgcct atgcaaatta ttcggcagca accaataagt cacaaattaa agatttaggg    960
caaaatggag taaagtagc agctggcgtt ccagtgacta agagtctga atggactggt     1020
aaaaactttg taccgccgtt aaaaacttta tatccgtcc aagataccta aactataat    1080
gacccaaccct gtggggagat gacctacatt tgctggccaa cagttgcgcc atcatctgct   1140
tatgtctata agggaggcaa aaaagcaatt tctggttggg aaaataccctt attggttcca  1200
tcttttaaagc gtggtgttat ttttcgtatt aagctagatc caacttacag tgctacttat  1260
gatgatgctg tgccgatgtt taagagcaac aatcgttatc gtgacgtgat tgcaagtcca   1320
gatggaaatg ttttatatgt attgactgat acttccggaa atgtccaaaa agatgatggt   1380
tctgtaacga atacattaga aaaccccagga tctctgatta gatttacata taaagctcag  1440
taa                                                                 1443
```

<210> SEQ ID NO 10
<211> LENGTH: 480
<212> TYPE: PRT
<213> ORGANISM: Acinetobacter sp.

<400> SEQUENCE: 10

| | | | | | | | | | | | | | | |
|---|---|---|---|---|---|---|---|---|---|---|---|---|---|---|
| Met | Asn | Lys | His | Leu | Leu | Ala | Lys | Ile | Thr | Leu | Leu | Gly | Ala | Ala | Gln |
| 1 | | | | 5 | | | | | 10 | | | | | 15 | |
| Leu | Leu | Thr | Leu | Asn | Ser | Ala | Phe | Ala | Asp | Val | Pro | Leu | Thr | Pro | Ser |
| | | | 20 | | | | | 25 | | | | | 30 | | |
| Gln | Phe | Ala | Lys | Ala | Lys | Thr | Glu | Ser | Phe | Asp | Lys | Lys | Val | Leu | Leu |
| | | | 35 | | | | | 40 | | | | | 45 | | |
| Ser | Asn | Leu | Asn | Lys | Pro | His | Ala | Leu | Leu | Trp | Gly | Pro | Asp | Asn | Gln |
| | 50 | | | | | 55 | | | | | 60 | | | | |
| Ile | Trp | Leu | Thr | Glu | Arg | Ala | Thr | Gly | Lys | Ile | Leu | Arg | Val | Asn | Pro |
| 65 | | | | | 70 | | | | | 75 | | | | | 80 |
| Glu | Ser | Gly | Ser | Val | Lys | Thr | Val | Phe | Gln | Val | Pro | Glu | Ile | Val | Asn |
| | | | | 85 | | | | | 90 | | | | | 95 | |
| Asp | Ala | Asp | Gly | Gln | Asn | Gly | Leu | Leu | Gly | Phe | Ala | Phe | His | Pro | Asp |
| | | | 100 | | | | | 105 | | | | | 110 | | |
| Phe | Lys | Asn | Asn | Pro | Tyr | Ile | Tyr | Val | Ser | Gly | Thr | Phe | Lys | Asn | Pro |
| | | | 115 | | | | | 120 | | | | | 125 | | |
| Lys | Ser | Thr | Asp | Lys | Glu | Leu | Pro | Asn | Gln | Thr | Ile | Ile | Arg | Arg | Tyr |
| | 130 | | | | | 135 | | | | | 140 | | | | |
| Thr | Tyr | Asn | Lys | Ala | Thr | Asp | Thr | Leu | Glu | Lys | Pro | Val | Asp | Leu | Leu |
| 145 | | | | | 150 | | | | | 155 | | | | | 160 |
| Ala | Gly | Leu | Pro | Ser | Ser | Lys | Asp | His | Gln | Ser | Gly | Arg | Leu | Val | Ile |
| | | | | 165 | | | | | 170 | | | | | 175 | |
| Gly | Pro | Asp | Gln | Lys | Ile | Tyr | Tyr | Thr | Ile | Gly | Asp | Gln | Gly | Arg | Asn |
| | | | 180 | | | | | 185 | | | | | 190 | | |
| Gln | Leu | Ala | Tyr | Leu | Phe | Leu | Pro | Asn | Gln | Ala | Gln | His | Thr | Pro | Thr |
| | | | 195 | | | | | 200 | | | | | 205 | | |
| Gln | Gln | Glu | Leu | Ser | Gly | Lys | Asp | Tyr | His | Thr | Tyr | Met | Gly | Lys | Val |
| | 210 | | | | | 215 | | | | | 220 | | | | |
| Leu | Arg | Leu | Asn | Leu | Asp | Gly | Ser | Ile | Pro | Lys | Asp | Asn | Pro | Ser | Phe |
| 225 | | | | | 230 | | | | | 235 | | | | | 240 |
| Asn | Gly | Val | Ile | Ser | His | Ile | Tyr | Thr | Leu | Gly | His | Arg | Asn | Pro | Gln |
| | | | | 245 | | | | | 250 | | | | | 255 | |
| Gly | Leu | Ala | Phe | Thr | Pro | Asn | Gly | Lys | Leu | Leu | Gln | Ser | Glu | Gln | Gly |
| | | | 260 | | | | | 265 | | | | | 270 | | |
| Pro | Asn | Ser | Asp | Asp | Glu | Ile | Asn | Leu | Ile | Val | Lys | Gly | Gly | Asn | Tyr |
| | | | 275 | | | | | 280 | | | | | 285 | | |
| Gly | Trp | Pro | Asn | Ala | Ala | Gly | Tyr | Lys | Asp | Asp | Ser | Gly | Tyr | Ala | Tyr |
| | 290 | | | | | 295 | | | | | 300 | | | | |
| Ala | Asn | Tyr | Ser | Ala | Ala | Thr | Asn | Lys | Ser | Gln | Ile | Lys | Asp | Leu | Gly |
| 305 | | | | | 310 | | | | | 315 | | | | | 320 |
| Gln | Asn | Gly | Val | Lys | Val | Ala | Ala | Gly | Val | Pro | Val | Thr | Lys | Glu | Ser |
| | | | | 325 | | | | | 330 | | | | | 335 | |
| Glu | Trp | Thr | Gly | Lys | Asn | Phe | Val | Pro | Pro | Leu | Lys | Thr | Leu | Tyr | Thr |
| | | | 340 | | | | | 345 | | | | | 350 | | |
| Val | Gln | Asp | Thr | Tyr | Asn | Tyr | Asn | Asp | Pro | Thr | Cys | Gly | Glu | Met | Thr |
| | | | 355 | | | | | 360 | | | | | 365 | | |
| Tyr | Ile | Cys | Trp | Pro | Thr | Val | Ala | Pro | Ser | Ser | Ala | Tyr | Val | Tyr | Lys |

```
                370             375             380
Gly Gly Lys Lys Ala Ile Ser Gly Trp Glu Asn Thr Leu Leu Val Pro
385                 390                 395                 400

Ser Leu Lys Arg Gly Val Ile Phe Arg Ile Lys Leu Asp Pro Thr Tyr
                405                 410                 415

Ser Ala Thr Tyr Asp Asp Ala Val Pro Met Phe Lys Ser Asn Asn Arg
            420                 425                 430

Tyr Arg Asp Val Ile Ala Ser Pro Asp Gly Asn Val Leu Tyr Val Leu
        435                 440                 445

Thr Asp Thr Ser Gly Asn Val Gln Lys Asp Asp Gly Ser Val Thr Asn
    450                 455                 460

Thr Leu Glu Asn Pro Gly Ser Leu Ile Arg Phe Thr Tyr Lys Ala Gln
465                 470                 475                 480

<210> SEQ ID NO 11
<211> LENGTH: 1443
<212> TYPE: DNA
<213> ORGANISM: Acinetobacter sp.

<400> SEQUENCE: 11
```

| | | | | | |
|---|---|---|---|---|---|
| atgaataaac | atttattggc | taaaattact | ttattaggtg | ctgctcagct | acttacgctc | 60 |
| aattcagcat | ttgctgatgt | ccctcttaca | ccatctcaat | ttgctaaagc | gaaacagaa | 120 |
| agctttgata | agaaagttct | tctatctaat | ttaaataagc | cacatgcttt | gttgtgggga | 180 |
| cctgataatc | aaatttggtt | aacggagcgg | gcaacaggta | agattctaag | agttaatcca | 240 |
| gagtcgggca | gtgtaaaaac | agttttcag | gttcctgaga | ttgtaaatga | tgctgatgga | 300 |
| caaaacggtt | tattgggttt | tgcctttcat | cctgacttta | aaaataatcc | ttatatctat | 360 |
| gtttcaggta | catttaaaaa | tccgaaatct | acagataaag | aattaccgaa | tcaaactatt | 420 |
| atccgtcgat | ataccatataa | caaggcaaca | gatacccttg | agaaaccagt | agatttattg | 480 |
| gcaggattac | cttcatcgaa | agaccatcag | tcgggtcgtc | ttgtgattgg | tccagaccaa | 540 |
| aagatttact | atacgattgg | tgatcaggga | cgtaaccagc | tggcttattt | attcttacca | 600 |
| aatcaagcac | agcatacgcc | gactcaacag | gaactgagcg | gcaaagacta | tcatacctat | 660 |
| atgggtaaag | tattgcgctt | aaatctggat | ggaagtattc | caaaagataa | tccaagcttt | 720 |
| aacggtgtaa | ttagccatat | tatacgctc | ggtcatcgta | acccacaggg | cttggcattt | 780 |
| actccaaatg | gtaaactgtt | gcaatctgaa | cagggtccaa | actctgatga | tgaaattaac | 840 |
| ctcattgtca | aaggtggtaa | ctatggctgg | ccaaatgtag | cgggttataa | agatgatagt | 900 |
| ggttatgcct | atgcaaatta | ttcggcagca | agcaataaag | cacaaattaa | agatttagga | 960 |
| caaaatggtt | taaaagtggc | ggcaggtgta | cctgtgatga | agagtctgat | atggactggt | 1020 |
| aaaaactttg | taccgccgtt | aaaaacttta | taccgtcc | aagataccta | taactataat | 1080 |
| gacccaactt | gtggggatat | gacctacatt | tgctggccaa | cggttgcgcc | gtcatctgct | 1140 |
| tatgtctata | agggaggcaa | aaaagcaatt | tctggttggg | aaaatacatt | attggttcca | 1200 |
| tctttaaagc | gcggtgttat | tttccgtatt | aagctagatc | caacttacag | tactacttat | 1260 |
| gatgatgctg | tgccgatgtt | taagagcaac | aatcgttatc | gtgacgtgat | tgcaagtcca | 1320 |
| gatgggaatg | ttttatatgt | attgactgat | acttccggaa | atgtccaaaa | agatgatggt | 1380 |
| tctgtaacga | atacattaga | aaacccagga | tctctgatta | gatttacata | taaagctcag | 1440 |
| taa | | | | | | 1443 |

<210> SEQ ID NO 12
<211> LENGTH: 480
<212> TYPE: PRT
<213> ORGANISM: Acinetobacter sp.

<400> SEQUENCE: 12

```
Met Asn Lys His Leu Leu Ala Lys Ile Thr Leu Leu Gly Ala Ala Gln
1               5                   10                  15

Leu Leu Thr Leu Asn Ser Ala Phe Ala Asp Val Pro Leu Thr Pro Ser
            20                  25                  30

Gln Phe Ala Lys Ala Lys Thr Glu Ser Phe Asp Lys Lys Val Leu Leu
        35                  40                  45

Ser Asn Leu Asn Lys Pro His Ala Leu Leu Trp Gly Pro Asp Asn Gln
    50                  55                  60

Ile Trp Leu Thr Glu Arg Ala Thr Gly Lys Ile Leu Arg Val Asn Pro
65                  70                  75                  80

Glu Ser Gly Ser Val Lys Thr Val Phe Gln Val Pro Glu Ile Val Asn
                85                  90                  95

Asp Ala Asp Gly Gln Asn Gly Leu Leu Gly Phe Ala Phe His Pro Asp
            100                 105                 110

Phe Lys Asn Asn Pro Tyr Ile Tyr Val Ser Gly Thr Phe Lys Asn Pro
        115                 120                 125

Lys Ser Thr Asp Lys Glu Leu Pro Asn Gln Thr Ile Ile Arg Arg Tyr
    130                 135                 140

Thr Tyr Asn Lys Ala Thr Asp Thr Leu Glu Lys Pro Val Asp Leu Leu
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
            180                 185                 190

Gln Leu Ala Tyr Leu Phe Leu Pro Asn Gln Ala Gln His Thr Pro Thr
        195                 200                 205

Gln Gln Glu Leu Ser Gly Lys Asp Tyr His Thr Tyr Met Gly Lys Val
    210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
                245                 250                 255

Gly Leu Ala Phe Thr Pro Asn Gly Lys Leu Leu Gln Ser Glu Gln Gly
            260                 265                 270

Pro Asn Ser Asp Asp Glu Ile Asn Leu Ile Val Lys Gly Gly Asn Tyr
        275                 280                 285

Gly Trp Pro Asn Val Ala Gly Tyr Lys Asp Asp Ser Gly Tyr Ala Tyr
    290                 295                 300

Ala Asn Tyr Ser Ala Ala Ser Asn Lys Ala Gln Ile Lys Asp Leu Gly
305                 310                 315                 320

Gln Asn Gly Leu Lys Val Ala Ala Gly Val Pro Val Met Lys Glu Ser
                325                 330                 335

Glu Trp Thr Gly Lys Asn Phe Val Pro Pro Leu Lys Thr Leu Tyr Thr
            340                 345                 350

Val Gln Asp Thr Tyr Asn Tyr Asn Asp Pro Thr Cys Gly Asp Met Thr
        355                 360                 365

Tyr Ile Cys Trp Pro Thr Val Ala Pro Ser Ser Ala Tyr Val Tyr Lys
    370                 375                 380
```

```
Gly Gly Lys Lys Ala Ile Ser Gly Trp Glu Asn Thr Leu Leu Val Pro
385                 390                 395                 400

Ser Leu Lys Arg Gly Val Ile Phe Arg Ile Lys Leu Asp Pro Thr Tyr
            405                 410                 415

Ser Thr Thr Tyr Asp Asp Ala Val Pro Met Phe Lys Ser Asn Asn Arg
                420                 425                 430

Tyr Arg Asp Val Ile Ala Ser Pro Asp Gly Asn Val Leu Tyr Val Leu
            435                 440                 445

Thr Asp Thr Ser Gly Asn Val Gln Lys Asp Asp Gly Ser Val Thr Asn
            450                 455                 460

Thr Leu Glu Asn Pro Gly Ser Leu Ile Arg Phe Thr Tyr Lys Ala Gln
465                 470                 475                 480

<210> SEQ ID NO 13
<211> LENGTH: 1443
<212> TYPE: DNA
<213> ORGANISM: Acinetobacter sp.

<400> SEQUENCE: 13
atgaataaac attttattggc taaaattact ttattaggtg ctgctcagct agttacgctc      60
aattcagcat tgctgatgt ccctcttact ccatctcaat ttgctaaagc gaaaacagga     120
agctttgaca agaaagttct tatatctaat ttaaataagc cacatgcttt gttgtggggg     180
cctgataatc aaatttggtt aacggagcgg gcaacaggta agattctaag agttaatcca     240
gagtcgggca gtgtaaaaac agttttcag gttcctgaga ttgtaaatga tgctgatgga     300
caaaacggtt tattgggttt tgcctttcat cctgacttta aaaataatcc ttatatctat     360
gtttcaggta catttaaaaa tccgaaatct acagataaag aattaccgaa tcaaactatt     420
atccgtcgat ataacctataa caaagcaaca gatactcttg agaaaccagt agatttattg     480
gcaggattac cttcatcgaa agaccatcag tcgggtcgcc ttgtcattgg tccagaccaa     540
aagatttact atacgattgg tgatcaggga cgtaaccagc ttgcttattt attcttacca     600
aatcaggcac aacatacgcc gactcaacag gaactgagcg aaaagacta tcataacctat     660 atgggtaaag tattacgctt aaatctggat ggaagtattc caaagataa tccaagcttt     720 aacggtgtaa ttagtcatat ttatacgctc ggtcatcgta atccacaggg cttggcattt     780
actccaaatg gtaaactgtt gcaatctgaa caaggtccaa actctgatga tgaaattaat     840
ctcattgtta aaggtggcaa ctatggctgg ccaaatgtag cgggttataa agatgacagt     900
ggttatgcct atgcaaatta ttcggcagca gccaataagt cacaaattaa agatttaggg     960
caaaatggag taaagtagc ggcaggtgta cctgtgatga agagtctga atggactggt    1020 aaaaactttg taccgccgtt aaaaacttta tataccgtcc aagataccta aactataat    1080 gacccaacct gtggggatat gacctacatt tgctggccaa cagttgcacc gtcatctgct   1140
tatgtctata agggcggcaa aaaagcaatt tctggttggg aaaatacatt attggttcca   1200 tcttttaaagc gtggtgttat tttccgtatt aagctagatc caacttacag tgctacttat   1260
gatgatgctg tgccgatgtt taagagcaac aatcgttatc gtgacgtgat tgcaagtcca   1320
gatgggaatg tttttatatgt attgactgat acttccggaa atgtccaaaa agatgatggt   1380
tctgtaacga atacattaga aaatccagga tctctgatta gatttacata taagctcag    1440 taa                                                                1443

<210> SEQ ID NO 14
<211> LENGTH: 480
```

```
<212> TYPE: PRT
<213> ORGANISM: Acinetobacter sp.

<400> SEQUENCE: 14

Met Asn Lys His Leu Leu Ala Lys Ile Thr Leu Leu Gly Ala Ala Gln
1               5                   10                  15

Leu Val Thr Leu Asn Ser Ala Phe Ala Asp Val Pro Leu Thr Pro Ser
            20                  25                  30

Gln Phe Ala Lys Ala Lys Thr Gly Ser Phe Asp Lys Lys Val Leu Ile
        35                  40                  45

Ser Asn Leu Asn Lys Pro His Ala Leu Leu Trp Gly Pro Asp Asn Gln
50                  55                  60

Ile Trp Leu Thr Glu Arg Ala Thr Gly Lys Ile Leu Arg Val Asn Pro
65                  70                  75                  80

Glu Ser Gly Ser Val Lys Thr Val Phe Gln Val Pro Glu Ile Val Asn
                85                  90                  95

Asp Ala Asp Gly Gln Asn Gly Leu Leu Gly Phe Ala Phe His Pro Asp
            100                 105                 110

Phe Lys Asn Asn Pro Tyr Ile Tyr Val Ser Gly Thr Phe Lys Asn Pro
        115                 120                 125

Lys Ser Thr Asp Lys Glu Leu Pro Asn Gln Thr Ile Ile Arg Arg Tyr
    130                 135                 140

Thr Tyr Asn Lys Ala Thr Asp Thr Leu Glu Lys Pro Val Asp Leu Leu
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
            180                 185                 190

Gln Leu Ala Tyr Leu Phe Leu Pro Asn Gln Ala Gln His Thr Pro Thr
        195                 200                 205

Gln Gln Glu Leu Ser Gly Lys Asp Tyr His Thr Tyr Met Gly Lys Val
    210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
                245                 250                 255

Gly Leu Ala Phe Thr Pro Asn Gly Lys Leu Leu Gln Ser Glu Gln Gly
            260                 265                 270

Pro Asn Ser Asp Asp Glu Ile Asn Leu Ile Val Lys Gly Gly Asn Tyr
        275                 280                 285

Gly Trp Pro Asn Val Ala Gly Tyr Lys Asp Asp Ser Gly Tyr Ala Tyr
    290                 295                 300

Ala Asn Tyr Ser Ala Ala Asn Lys Ser Gln Ile Lys Asp Leu Gly
305                 310                 315                 320

Gln Asn Gly Val Lys Val Ala Ala Gly Val Pro Val Met Lys Glu Ser
                325                 330                 335

Glu Trp Thr Gly Lys Asn Phe Val Pro Pro Leu Lys Thr Leu Tyr Thr
            340                 345                 350

Val Gln Asp Thr Tyr Asn Tyr Asn Asp Pro Thr Cys Gly Asp Met Thr
        355                 360                 365

Tyr Ile Cys Trp Pro Thr Val Ala Pro Ser Ser Ala Tyr Val Tyr Lys
    370                 375                 380

Gly Gly Lys Lys Ala Ile Ser Gly Trp Glu Asn Thr Leu Leu Val Pro
385                 390                 395                 400
```

-continued

Ser Leu Lys Arg Gly Val Ile Phe Arg Ile Lys Leu Asp Pro Thr Tyr
            405                 410                 415

Ser Ala Thr Tyr Asp Asp Ala Val Pro Met Phe Lys Ser Asn Asn Arg
            420                 425                 430

Tyr Arg Asp Val Ile Ala Ser Pro Asp Gly Asn Val Leu Tyr Val Leu
            435                 440                 445

Thr Asp Thr Ser Gly Asn Val Gln Lys Asp Asp Gly Ser Val Thr Asn
        450                 455                 460

Thr Leu Glu Asn Pro Gly Ser Leu Ile Arg Phe Thr Tyr Lys Ala Gln
465                 470                 475                 480

<210> SEQ ID NO 15
<211> LENGTH: 1443
<212> TYPE: DNA
<213> ORGANISM: Acinetobacter sp.

<400> SEQUENCE: 15

| | | |
|---|---|---|
| atgaataaac atttattggc taaaattact ttattaggtg ctgctcagtt acttacgctc | 60 |
| aattcagcat ttgctgatgt ccctcttacc ccatctcaat ttgctaaagc gaaaacagaa | 120 |
| agctttgaca agaaagttct tctatctaat ttaaataagc cacatgcttt gttgtgggga | 180 |
| cctgataatc aaatttggtt aacggagcgg gcaacaggta agattctaag agttaatcca | 240 |
| gagtcgggca gtgtaaaaac agttttcag gttcctgaga ttgtaagtga tgctgatgga | 300 |
| caaaacggtt tattgggttt tgcctttcat actgacttta aaataatcc ttatatctat | 360 |
| gtttcaggta catttaaaaa tccgaaatct acagataaag aattaccgaa tcaaactatt | 420 |
| atccgtcgat atacctataa caaagcaaca gatactcttg agaaaccagt agatttatta | 480 |
| gcaggattac cttcatcgaa agaccatcag tcgggtcgtc ttgtcattgg tccagaccaa | 540 |
| aagatttact atacgattgg tgatcaggga cgtaaccagc ttgcttattt attcttacca | 600 |
| aatcaggcac aacatacgcc gactcaacag gaactgagcg gcaaagacta tcatacctat | 660 |
| atgggtaaag tattacgctt aaatctggat ggaagtattc aaaagataa tccaagcttt | 720 |
| aacggtgtaa ttagccatat ttatacgctc ggtcatcgta acccacaggg cttggcattt | 780 |
| actccaaatg gtaaactgtt gcaatctgaa cagggtccaa actctgacga tgaaattaat | 840 |
| ctcattgtta aaggtggtaa ctatggctgg ccaaatgtag cgggttataa agatgacagt | 900 |
| ggttatgcct atgcaaatta ttcggcagca accaataagt cacaaattaa agatttaggg | 960 |
| caaaatggag taaagtagc ggcaggtgta cctgtgatga aagagtctga atggactggt | 1020 |
| aaaaactttg taccgccgtt aaaaacttta tataccgtcc aagataccta taactataat | 1080 |
| gacccaactt gtggggatat gacctacatt tgctggccaa cggttgcgcc gtcatctgct | 1140 |
| tatgtctata agggaggcaa aaaagcaatt tctggttggg aaaatacatt attggttcca | 1200 |
| tctttaaagc gcggtgttat tttccgtatt aagctagatc aacttacag tgctactat | 1260 |
| gatgatgctg tgccgatgtt taaaagcaac aatcgttatc gtgacgtgat tgcaagtcca | 1320 |
| gatgggaatg ttttatatgt attgactgat acttccggaa atgtccaaaa agatgatggt | 1380 |
| tctgtaacga atacattaga aaatccagga tccctgatta gatttacata taagctcag | 1440 |
| taa | 1443 |

<210> SEQ ID NO 16
<211> LENGTH: 480
<212> TYPE: PRT
<213> ORGANISM: Acinetobacter sp.

<400> SEQUENCE: 16

```
Met Asn Lys His Leu Leu Ala Lys Ile Thr Leu Leu Gly Ala Ala Gln
1               5                   10                  15

Leu Leu Thr Leu Asn Ser Ala Phe Ala Asp Val Pro Leu Thr Pro Ser
            20                  25                  30

Gln Phe Ala Lys Ala Lys Thr Glu Ser Phe Asp Lys Lys Val Leu Leu
        35                  40                  45

Ser Asn Leu Asn Lys Pro His Ala Leu Leu Trp Gly Pro Asp Asn Gln
    50                  55                  60

Ile Trp Leu Thr Glu Arg Ala Thr Gly Lys Ile Leu Arg Val Asn Pro
65                  70                  75                  80

Glu Ser Gly Ser Val Lys Thr Val Phe Gln Val Pro Glu Ile Val Ser
                85                  90                  95

Asp Ala Asp Gly Gln Asn Gly Leu Leu Gly Phe Ala Phe His Thr Asp
            100                 105                 110

Phe Lys Asn Asn Pro Tyr Ile Tyr Val Ser Gly Thr Phe Lys Asn Pro
        115                 120                 125

Lys Ser Thr Asp Lys Glu Leu Pro Asn Gln Thr Ile Ile Arg Arg Tyr
    130                 135                 140

Thr Tyr Asn Lys Ala Thr Asp Thr Leu Glu Lys Pro Val Asp Leu Leu
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
            180                 185                 190

Gln Leu Ala Tyr Leu Phe Leu Pro Asn Gln Ala Gln His Thr Pro Thr
        195                 200                 205

Gln Gln Glu Leu Ser Gly Lys Asp Tyr His Thr Tyr Met Gly Lys Val
    210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
                245                 250                 255

Gly Leu Ala Phe Thr Pro Asn Gly Lys Leu Leu Gln Ser Glu Gln Gly
            260                 265                 270

Pro Asn Ser Asp Asp Glu Ile Asn Leu Ile Val Lys Gly Gly Asn Tyr
        275                 280                 285

Gly Trp Pro Asn Val Ala Gly Tyr Lys Asp Asp Ser Gly Tyr Ala Tyr
    290                 295                 300

Ala Asn Tyr Ser Ala Ala Thr Asn Lys Ser Gln Ile Lys Asp Leu Gly
305                 310                 315                 320

Gln Asn Gly Val Lys Val Ala Ala Gly Val Pro Val Met Lys Glu Ser
                325                 330                 335

Glu Trp Thr Gly Lys Asn Phe Val Pro Pro Leu Lys Thr Leu Tyr Thr
            340                 345                 350

Val Gln Asp Thr Tyr Asn Tyr Asn Asp Pro Thr Cys Gly Asp Met Thr
        355                 360                 365

Tyr Ile Cys Trp Pro Thr Val Ala Pro Ser Ser Ala Tyr Val Tyr Lys
    370                 375                 380

Gly Gly Lys Lys Ala Ile Ser Gly Trp Glu Asn Thr Leu Leu Val Pro
385                 390                 395                 400

Ser Leu Lys Arg Gly Val Ile Phe Arg Ile Lys Leu Asp Pro Thr Tyr
```

```
                    405                 410                 415
Ser Ala Thr Tyr Asp Asp Ala Val Pro Met Phe Lys Ser Asn Asn Arg
            420                 425                 430

Tyr Arg Asp Val Ile Ala Ser Pro Asp Gly Asn Val Leu Tyr Val Leu
            435                 440                 445

Thr Asp Thr Ser Gly Asn Val Gln Lys Asp Asp Gly Ser Val Thr Asn
            450                 455                 460

Thr Leu Glu Asn Pro Gly Ser Leu Ile Arg Phe Thr Tyr Lys Ala Gln
465                 470                 475                 480

<210> SEQ ID NO 17
<211> LENGTH: 1443
<212> TYPE: DNA
<213> ORGANISM: Acinetobacter sp.

<400> SEQUENCE: 17
atgaataaac atttattggc taaaattact ttattaggtg ctgctcagct acttacgctc     60
aattcagcat ttgctgatgt ccctcttact ccatctcaat ttgctaaagc gaaaacagaa    120
agctttgaca agaaagttct tctatctaat ttaaataagc cacatgcttt gttgtgggga    180
cctgataatc aaatttggtt aacggagcgg gcaacaggta agattctaag agttaaccct    240
gaatcaggca gtgtaaaaac agttttcag gttcctgaga ttgtaaatga tgctgatgga    300
caaaacggtt tattgggttt tgcctttcat cctgactttta aacataatcc ttatatctat    360
gtttcaggta catttaaaaa tccgaaatct acagataaag aattaccgaa tcaaactatt    420
atccgtcgat ataccctataa caaggcaaca gatacccttg agaaaccagt agatttatta    480
gcaggattac cttcatcgaa agaccatcag tcgggtcgtc ttgtgattgg tccagaccaa    540
aagatttact atacgattgg tgatcagggg cgtaaccagc tggcttattt attcttgcca    600
aatcaagcac agcatacgcc gactcaacaa gagctgagcg gtaaagacta tcacacctat    660
atgggtaaag tattacgctt aaatctagat ggaagtattc caaaagataa tccaagcttt    720
aacggtgtaa ttagccatat ttatacactc ggtcatcgta atccacaggg cttggccttt    780
actccaaatg gtaaactgtt gcaatctgaa caaggtccaa actctgatga tgaaattaat    840
ctgattgtta aggtggtaa ctatggctgg ccaaatgtag cgggttataa agatgacagt    900
ggttatgcct atgcaaatta ttcggcagca accaataagt cacaaattaa agatttaggg    960
caaaatggag taaagtagc ggcaggtgta cctgtaatga agagtctga atggactggt    1020 aaaaactttg taccgccgtt aaaaacttta tataccgtcc aagataccta taactataat    1080
gacccaacct gtggggatat gacctacatt tgctggccaa cggttgcgcc gtcatctgct    1140
tatgtctata agggaggcaa aaaagcaatt tctggttggg aaaataccctt attggttcca    1200 tctttaaagc gcggtgttat tttccgtatt aagctagatc aacttacag tgctacttat    1260 gatgatgctg tgccgatgtt taagagcaac aatcgttatc gtgacgtgat tgcaagtcca    1320
gatggaaatg tttatatgt attgactgat acttccggaa atgtccaaaa agatgatggc    1380
tctgtaacga atacattaga aaatccagga tctttgatta ggtttacata taagctcag    1440 taa                                                                  1443

<210> SEQ ID NO 18
<211> LENGTH: 480
<212> TYPE: PRT
<213> ORGANISM: Acinetobacter sp.

<400> SEQUENCE: 18
```

```
Met Asn Lys His Leu Leu Ala Lys Ile Thr Leu Leu Gly Ala Ala Gln
1               5                   10                  15

Leu Leu Thr Leu Asn Ser Ala Phe Ala Asp Val Pro Leu Thr Pro Ser
            20                  25                  30

Gln Phe Ala Lys Ala Lys Thr Glu Ser Phe Asp Lys Lys Val Leu Leu
        35                  40                  45

Ser Asn Leu Asn Lys Pro His Ala Leu Leu Trp Gly Pro Asp Asn Gln
    50                  55                  60

Ile Trp Leu Thr Glu Arg Ala Thr Gly Lys Ile Leu Arg Val Asn Pro
65                  70                  75                  80

Glu Ser Gly Ser Val Lys Thr Val Phe Gln Val Pro Glu Ile Val Asn
                85                  90                  95

Asp Ala Asp Gly Gln Asn Gly Leu Leu Gly Phe Ala Phe His Pro Asp
            100                 105                 110

Phe Lys His Asn Pro Tyr Ile Tyr Val Ser Gly Thr Phe Lys Asn Pro
        115                 120                 125

Lys Ser Thr Asp Lys Glu Leu Pro Asn Gln Thr Ile Ile Arg Arg Tyr
    130                 135                 140

Thr Tyr Asn Lys Ala Thr Asp Thr Leu Glu Lys Pro Val Asp Leu Leu
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
            180                 185                 190

Gln Leu Ala Tyr Leu Phe Leu Pro Asn Gln Ala Gln His Thr Pro Thr
        195                 200                 205

Gln Gln Glu Leu Ser Gly Lys Asp Tyr His Thr Tyr Met Gly Lys Val
    210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
                245                 250                 255

Gly Leu Ala Phe Thr Pro Asn Gly Lys Leu Leu Gln Ser Glu Gln Gly
            260                 265                 270

Pro Asn Ser Asp Asp Glu Ile Asn Leu Ile Val Lys Gly Gly Asn Tyr
        275                 280                 285

Gly Trp Pro Asn Val Ala Gly Tyr Lys Asp Asp Ser Gly Tyr Ala Tyr
    290                 295                 300

Ala Asn Tyr Ser Ala Ala Thr Asn Lys Ser Gln Ile Lys Asp Leu Gly
305                 310                 315                 320

Gln Asn Gly Val Lys Val Ala Ala Gly Val Pro Val Met Lys Glu Ser
                325                 330                 335

Glu Trp Thr Gly Lys Asn Phe Val Pro Pro Leu Lys Thr Leu Tyr Thr
            340                 345                 350

Val Gln Asp Thr Tyr Asn Tyr Asn Asp Pro Thr Cys Gly Asp Met Thr
        355                 360                 365

Tyr Ile Cys Trp Pro Thr Val Ala Pro Ser Ser Ala Tyr Val Tyr Lys
    370                 375                 380

Gly Gly Lys Lys Ala Ile Ser Gly Trp Glu Asn Thr Leu Leu Val Pro
385                 390                 395                 400

Ser Leu Lys Arg Gly Val Ile Phe Arg Ile Lys Leu Asp Pro Thr Tyr
                405                 410                 415
```

```
Ser Ala Thr Tyr Asp Asp Ala Val Pro Met Phe Lys Ser Asn Asn Arg
            420                 425                 430

Tyr Arg Asp Val Ile Ala Ser Pro Asp Gly Asn Val Leu Tyr Val Leu
        435                 440                 445

Thr Asp Thr Ser Gly Asn Val Gln Lys Asp Asp Gly Ser Val Thr Asn
    450                 455                 460

Thr Leu Glu Asn Pro Gly Ser Leu Ile Arg Phe Thr Tyr Lys Ala Gln
465                 470                 475                 480

<210> SEQ ID NO 19
<211> LENGTH: 1443
<212> TYPE: DNA
<213> ORGANISM: Acinetobacter sp.

<400> SEQUENCE: 19
atgaataaac atttattggc taaaattact ttattaggtg ctgctcacct acttacgctc    60
aattcagcat ttgctgatgt ccctcttact ccatctcaat ttgctaaagc gaaaacagaa   120
agctttgaca agaaagttct tctatctaat ttaaataagc cgcatgcttt gttgtgggga   180
cctgataatc aaatttggtt aacagagcgg gcaacaggta agattctaag agttaaccct   240
gaatcaggca gtgtaaaaac agttttcag gttcctgaga ttgtaaatga tgctgatgga   300
caaaacggtt tattgggttt tgcctttcat cctgacttta acataatcc ttatatctat   360 gtttcaggta catttaaaaa tccgaaatct acagataaag aattaccgaa tcaaactatt   420
attcgtcgat atacctataa caaagcaaca gatactcttg ataaaccagt agatttatta   480
gcaggattac cttcatcgaa agaccatcag tcgggtcgtc ttgtgattgg ccagaccaa    540 aagatttact atacgattgg tgatcagggg cgtaaccagc tggcttattt attcttacca   600
aatcaggcac aacatacgcc gactcaacag gaactgagcg gcaaagacta tcatacctat   660
atgggtaaag tattacgctt aaatctggat ggaagtattc aaaagataa tccaagcttt   720 aacggtgtaa ttagccatat ttatacgctc ggtcatcgta acccacaggg cttggcattt   780
actccaaatg gtaaactgtt acaatctgaa cagggtccaa actctgacga tgaaattaat   840
ctcattgtta aaggtggtaa ctatggctgg ccaaatgtag cgggttataa agatgacagt   900
ggttatgcgt atgcaaatta ttcagcagca accaataagt cacaaattaa agatttaggg   960
caaaatggag taaagtagc ggcaggtgta cctgtgatga agagtctga atggactggt    1020 aaaaactttg taccgccgtt aaaaacttta tataccgtcc aagataccta taactataat  1080
gacccaactt gtggggatat gacctacatt tgctggccaa cagttgcgcc atcatctgct  1140
tatgtctata agggggggcaa aaaagcaatt tctggttggg aaaatacatt attggttcca  1200
tctttaaagc gtggtgttat ttttcgtatt aagctagatc caacttacag tactactat   1260 gatgatgctg tgccgatgtt taagagcaac aatcgttatc gtgacgtgat tgcaagtcca  1320
gatgggaatg ttttatatgt attgactgat acttccggaa atgtccaaaa agatgatggt  1380
tctgtaacga atacattaga aaacccagga tctctgatta gatttacata taaagctcag  1440
taa                                                                1443

<210> SEQ ID NO 20
<211> LENGTH: 480
<212> TYPE: PRT
<213> ORGANISM: Acinetobacter sp.

<400> SEQUENCE: 20

Met Asn Lys His Leu Leu Ala Lys Ile Thr Leu Leu Gly Ala Ala His
```

-continued

```
1               5                   10                  15

Leu Leu Thr Leu Asn Ser Ala Phe Ala Asp Val Pro Leu Thr Pro Ser
            20                  25                  30

Gln Phe Ala Lys Ala Lys Thr Glu Ser Phe Asp Lys Lys Val Leu Leu
            35                  40                  45

Ser Asn Leu Asn Lys Pro His Ala Leu Leu Trp Gly Pro Asp Asn Gln
            50                  55                  60

Ile Trp Leu Thr Glu Arg Ala Thr Gly Lys Ile Leu Arg Val Asn Pro
65                  70                  75                  80

Glu Ser Gly Ser Val Lys Thr Val Phe Gln Val Pro Glu Ile Val Asn
            85                  90                  95

Asp Ala Asp Gly Gln Asn Gly Leu Leu Gly Phe Ala Phe His Pro Asp
            100                 105                 110

Phe Lys His Asn Pro Tyr Ile Tyr Val Ser Gly Thr Phe Lys Asn Pro
            115                 120                 125

Lys Ser Thr Asp Lys Glu Leu Pro Asn Gln Thr Ile Ile Arg Arg Tyr
            130                 135                 140

Thr Tyr Asn Lys Ala Thr Asp Thr Leu Asp Lys Pro Val Asp Leu Leu
145                 150                 155                 160

Ala Gly Leu Pro Ser Ser Lys Asp His Gln Ser Gly Arg Leu Val Ile
            165                 170                 175

Gly Pro Asp Gln Lys Ile Tyr Tyr Thr Ile Gly Asp Gln Gly Arg Asn
            180                 185                 190

Gln Leu Ala Tyr Leu Phe Leu Pro Asn Gln Ala Gln His Thr Pro Thr
            195                 200                 205

Gln Gln Glu Leu Ser Gly Lys Asp Tyr His Thr Tyr Met Gly Lys Val
            210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
            245                 250                 255

Gly Leu Ala Phe Thr Pro Asn Gly Lys Leu Leu Gln Ser Glu Gln Gly
            260                 265                 270

Pro Asn Ser Asp Asp Glu Ile Asn Leu Ile Val Lys Gly Gly Asn Tyr
            275                 280                 285

Gly Trp Pro Asn Val Ala Gly Tyr Lys Asp Asp Ser Gly Tyr Ala Tyr
            290                 295                 300

Ala Asn Tyr Ser Ala Ala Thr Asn Lys Ser Gln Ile Lys Asp Leu Gly
305                 310                 315                 320

Gln Asn Gly Val Lys Val Ala Ala Gly Val Pro Val Met Lys Glu Ser
            325                 330                 335

Glu Trp Thr Gly Lys Asn Phe Val Pro Pro Leu Lys Thr Leu Tyr Thr
            340                 345                 350

Val Gln Asp Thr Tyr Asn Tyr Asn Asp Pro Thr Cys Gly Asp Met Thr
            355                 360                 365

Tyr Ile Cys Trp Pro Thr Val Ala Pro Ser Ser Ala Tyr Val Tyr Lys
            370                 375                 380

Gly Gly Lys Lys Ala Ile Ser Gly Trp Glu Asn Thr Leu Leu Val Pro
385                 390                 395                 400

Ser Leu Lys Arg Gly Val Ile Phe Arg Ile Lys Leu Asp Pro Thr Tyr
            405                 410                 415

Ser Thr Thr Tyr Asp Asp Ala Val Pro Met Phe Lys Ser Asn Asn Arg
            420                 425                 430
```

```
Tyr Arg Asp Val Ile Ala Ser Pro Asp Gly Asn Val Leu Tyr Val Leu
        435                 440                 445

Thr Asp Thr Ser Gly Asn Val Gln Lys Asp Asp Gly Ser Val Thr Asn
    450                 455                 460

Thr Leu Glu Asn Pro Gly Ser Leu Ile Arg Phe Thr Tyr Lys Ala Gln
465                 470                 475                 480

<210> SEQ ID NO 21
<211> LENGTH: 1443
<212> TYPE: DNA
<213> ORGANISM: Acinetobacter sp.

<400> SEQUENCE: 21
```

| | | | | | |
|---|---|---|---|---|---|
| atgaataaac | atttattggc | taaaattact | ttattaggtg | ctgctcagct | acttacgctc | 60 |
| aattcagcat | tgctgatgt | ccctcttaca | ccatctcaat | tgctaaagc | gaaaacagaa | 120 |
| agctttgaca | agaaagttct | tctatctaat | ttaaataagc | cacatgcttt | gttgtggggg | 180 |
| cctgataatc | aaatttggtt | aacggagcgg | gcaacaggta | agattctaag | agtgaatcca | 240 |
| gagtcgggca | gtgtaaaaac | agttttcag | gttcctgaga | ttgtaaatga | tgctgatgga | 300 |
| caaaacggtt | tattgggttt | tgcctttcat | cctgactta | aaaataatcc | ttatatctat | 360 |
| gtttcaggta | cttttaaaaa | tccgaaatct | acagataaag | aattaccgaa | tcaaactatt | 420 |
| attcgtcgat | atacctataa | caaagcaaca | gatactcttg | ataaaccagt | agatttatta | 480 |
| gcaggattac | cttcatcgaa | agaccatcag | tcgggtcgcc | ttgtgattgg | tccagaccaa | 540 |
| aagatttact | atacgattgg | tgatcagggg | cgtaaccagc | ttgcttattt | attcttacca | 600 |
| aatcaggcac | aacatacgcc | gactcaacag | gaactgagcg | gcaaagacta | tcatacctat | 660 |
| atgggtaaag | tattacgctt | aaatctggat | ggaagtattc | caaaagataa | tccaagcttt | 720 |
| aacggtgtaa | ttagccatat | ttatacgctc | ggtcatcgta | acccacaggg | cttggcattt | 780 |
| actccaaatg | gtaaactgtt | gcaatctgaa | cagggtccaa | actctgatga | tgaaattaac | 840 |
| ctcattgtca | aggtggtaa | ctatggctgg | ccaaatgtag | cgggttataa | agatgatagt | 900 |
| ggttatgcct | atgcaaatta | ttcagcagca | agcaataaag | cacaaattaa | agatttagga | 960 |
| caaaatggtt | taaagtggc | agctggcgtt | ccagtgacta | agagtctga | atggactggt | 1020 |
| aaaaactttg | taccgccgtt | aaaaacttta | tataccgtcc | aagataccta | taactataat | 1080 |
| gacccaacct | gtggggatat | gacctacatt | tgctggccaa | cggttgcgcc | gtcatctgct | 1140 |
| tatgtctata | agggaggcaa | aaaagcaatt | tctggttggg | aaaatacctt | attggttcca | 1200 |
| tctttaaagc | gcggtgttat | tttccgtatt | aagctagatc | caacttacag | tgctacttat | 1260 |
| gatgatgctg | tgccgatgtt | taagagcaac | aatcgttatc | gtgacgtgat | tgcaagtcca | 1320 |
| gatggaaatg | ttttatatgt | attgactgat | acttccggaa | atgtccaaaa | agatgatggt | 1380 |
| tctgtaacga | atacattaga | aaacccagga | tctctgatta | gatttacata | taagctcag | 1440 |
| taa | | | | | | 1443 |

```
<210> SEQ ID NO 22
<211> LENGTH: 480
<212> TYPE: PRT
<213> ORGANISM: Acinetobacter sp.

<400> SEQUENCE: 22

Met Asn Lys His Leu Leu Ala Lys Ile Thr Leu Leu Gly Ala Ala Gln
1               5                   10                  15
```

```
Leu Leu Thr Leu Asn Ser Ala Phe Ala Asp Val Pro Leu Thr Pro Ser
             20                  25                  30

Gln Phe Ala Lys Ala Lys Thr Glu Ser Phe Asp Lys Lys Val Leu Leu
         35                  40                  45

Ser Asn Leu Asn Lys Pro His Ala Leu Leu Trp Gly Pro Asp Asn Gln
     50                  55                  60

Ile Trp Leu Thr Glu Arg Ala Thr Gly Lys Ile Leu Arg Val Asn Pro
 65                  70                  75                  80

Glu Ser Gly Ser Val Lys Thr Val Phe Gln Val Pro Glu Ile Val Asn
                 85                  90                  95

Asp Ala Asp Gly Gln Asn Gly Leu Leu Gly Phe Ala Phe His Pro Asp
             100                 105                 110

Phe Lys Asn Asn Pro Tyr Ile Tyr Val Ser Gly Thr Phe Lys Asn Pro
         115                 120                 125

Lys Ser Thr Asp Lys Glu Leu Pro Asn Gln Thr Ile Ile Arg Arg Tyr
 130                 135                 140

Thr Tyr Asn Lys Ala Thr Asp Thr Leu Asp Lys Pro Val Asp Leu Leu
145                 150                 155                 160

Ala Gly Leu Pro Ser Ser Lys Asp His Gln Ser Gly Arg Leu Val Ile
                 165                 170                 175

Gly Pro Asp Gln Lys Ile Tyr Tyr Thr Ile Gly Asp Gln Gly Arg Asn
             180                 185                 190

Gln Leu Ala Tyr Leu Phe Leu Pro Asn Gln Ala Gln His Thr Pro Thr
         195                 200                 205

Gln Gln Glu Leu Ser Gly Lys Asp Tyr His Thr Tyr Met Gly Lys Val
 210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
                 245                 250                 255

Gly Leu Ala Phe Thr Pro Asn Gly Lys Leu Leu Gln Ser Glu Gln Gly
             260                 265                 270

Pro Asn Ser Asp Asp Glu Ile Asn Leu Ile Val Lys Gly Gly Asn Tyr
         275                 280                 285

Gly Trp Pro Asn Val Ala Gly Tyr Lys Asp Asp Ser Gly Tyr Ala Tyr
 290                 295                 300

Ala Asn Tyr Ser Ala Ala Ser Asn Lys Ala Gln Ile Lys Asp Leu Gly
305                 310                 315                 320

Gln Asn Gly Leu Lys Val Ala Ala Gly Val Pro Val Thr Lys Glu Ser
                 325                 330                 335

Glu Trp Thr Gly Lys Asn Phe Val Pro Pro Leu Lys Thr Leu Tyr Thr
             340                 345                 350

Val Gln Asp Thr Tyr Asn Tyr Asn Asp Pro Thr Cys Gly Asp Met Thr
         355                 360                 365

Tyr Ile Cys Trp Pro Thr Val Ala Pro Ser Ser Ala Tyr Val Tyr Lys
 370                 375                 380

Gly Gly Lys Lys Ala Ile Ser Gly Trp Glu Asn Thr Leu Leu Val Pro
385                 390                 395                 400

Ser Leu Lys Arg Gly Val Ile Phe Arg Ile Lys Leu Asp Pro Thr Tyr
                 405                 410                 415

Ser Ala Thr Tyr Asp Asp Ala Val Pro Met Phe Lys Ser Asn Asn Arg
         420                 425                 430

Tyr Arg Asp Val Ile Ala Ser Pro Asp Gly Asn Val Leu Tyr Val Leu
```

```
            435             440             445
Thr Asp Thr Ser Gly Asn Val Gln Lys Asp Asp Gly Ser Val Thr Asn
    450                 455                 460

Thr Leu Glu Asn Pro Gly Ser Leu Ile Arg Phe Thr Tyr Lys Ala Gln
465                 470                 475                 480
```

<210> SEQ ID NO 23
<211> LENGTH: 1443
<212> TYPE: DNA
<213> ORGANISM: Acinetobacter sp.

<400> SEQUENCE: 23

```
atgaataaac atttattggc taaaattact ttattaggtg ctgctcagct acttacactc      60
aattcagcat ttgctgatgt ccctcttaca ccatctcaat ttgctaaagc gaaaacagaa     120
agctttgaca agaaagttct tctatctaat ttaaataagc cacatgcttt gttgtggggg     180
cctgataatc aaatttggtt aacggagcgg gcaacaggta agattctaag agtgaatcca     240
gagtcgggca gtgtaaaaac agttttcag gttcctgaga ttgtaaatga tgctgatgga      300
caaaacggtt tattgggttt tgcctttcat cctgactta aaaataatcc ttatatctat       360
gtttcaggta cttttaaaaa tccgaaatct acagataaag aattaccgaa tcaaactatt     420
attcgtcgat atacctataa caaagcaaca gatactcttg ataaaccagt agatttatta     480
gcaggattac cttcatcgaa agaccatcag tcgggtcgcc ttgtgattgg tccagaccaa     540
aaaatttact atacgattgg tgatcagggg cgtaaccagc ttgcttattt attcttacca     600
aatcaggcac aacatacgcc gactcaacag gaactgagcg gcaaagacta tcatacctat     660
atgggtaaag tattacgctt aaatctggat ggaagtattc aaaagataa tccaagcttt     720
aacggtgtaa ttagtcatat ttatacgctc ggtcatcgta atccacaggg cttagcattc     780
actccaaatg gtaaactgtt gcaatctgaa caaggtccaa actctgatga tgaaattaat     840
ctcattgtta aaggtggtaa ctatggctgg ccaaatgtag ctggttataa agatgatagt     900
ggttatgcct atgcaaatta ttcagcagca agcaataaag cacaaattaa agatttagga     960
caaaatggtt taaaagtggc agctggcgtt ccagtgacta agagtctga atggactggt     1020
aaaaactttg taccgccgtt aaaaacttta tataccgtcc aagataccta aactataat     1080
gacccaacct gtggggatat gacctacatt tgctggccaa cggttgcgcc gtcatctgct     1140
tatgtctata agggaggcaa aaaagcaatt tctggttggg aaaataccctt attggttcca    1200
tctttaaagc gcggtgttat tttccgtatt aagctagatc caacttacaa tactactat     1260
gatgatgctg tgccgatgtt taagagcaac aatcgttatc gtgacgtgat tgcaagtcca    1320
gatggaaatg tttatatgt attgactgat acttccggaa atgtccaaaa agatgatggc     1380
tctgtaacga atacattaga aaacccagga tctctgatta gatttacata taaagctcag    1440
taa                                                                  1443
```

<210> SEQ ID NO 24
<211> LENGTH: 480
<212> TYPE: PRT
<213> ORGANISM: Acinetobacter sp.

<400> SEQUENCE: 24

```
Met Asn Lys His Leu Leu Ala Lys Ile Thr Leu Leu Gly Ala Ala Gln
1               5                   10                  15

Leu Leu Thr Leu Asn Ser Ala Phe Ala Asp Val Pro Leu Thr Pro Ser
            20                  25                  30
```

```
Gln Phe Ala Lys Ala Lys Thr Glu Ser Phe Asp Lys Val Leu Leu
            35                  40                  45

Ser Asn Leu Asn Lys Pro His Ala Leu Leu Trp Gly Pro Asp Asn Gln
 50                  55                  60

Ile Trp Leu Thr Glu Arg Ala Thr Gly Lys Ile Leu Arg Val Asn Pro
 65                  70                  75                  80

Glu Ser Gly Ser Val Lys Thr Val Phe Gln Val Pro Glu Ile Val Asn
                 85                  90                  95

Asp Ala Asp Gly Gln Asn Gly Leu Leu Gly Phe Ala Phe His Pro Asp
            100                 105                 110

Phe Lys Asn Asn Pro Tyr Ile Tyr Val Ser Gly Thr Phe Lys Asn Pro
            115                 120                 125

Lys Ser Thr Asp Lys Glu Leu Pro Asn Gln Thr Ile Ile Arg Arg Tyr
130                 135                 140

Thr Tyr Asn Lys Ala Thr Asp Thr Leu Asp Lys Pro Val Asp Leu Leu
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
            180                 185                 190

Gln Leu Ala Tyr Leu Phe Leu Pro Asn Gln Ala Gln His Thr Pro Thr
            195                 200                 205

Gln Gln Glu Leu Ser Gly Lys Asp Tyr His Thr Tyr Met Gly Lys Val
210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
                245                 250                 255

Gly Leu Ala Phe Thr Pro Asn Gly Lys Leu Leu Gln Ser Glu Gln Gly
            260                 265                 270

Pro Asn Ser Asp Asp Glu Ile Asn Leu Ile Val Lys Gly Gly Asn Tyr
            275                 280                 285

Gly Trp Pro Asn Val Ala Gly Tyr Lys Asp Asp Ser Gly Tyr Ala Tyr
290                 295                 300

Ala Asn Tyr Ser Ala Ala Ser Asn Lys Ala Gln Ile Lys Asp Leu Gly
305                 310                 315                 320

Gln Asn Gly Leu Lys Val Ala Ala Gly Val Pro Val Thr Lys Glu Ser
                325                 330                 335

Glu Trp Thr Gly Lys Asn Phe Val Pro Pro Leu Lys Thr Leu Tyr Thr
            340                 345                 350

Val Gln Asp Thr Tyr Asn Tyr Asn Asp Pro Thr Cys Gly Asp Met Thr
            355                 360                 365

Tyr Ile Cys Trp Pro Thr Val Ala Pro Ser Ser Ala Tyr Val Tyr Lys
370                 375                 380

Gly Gly Lys Lys Ala Ile Ser Gly Trp Glu Asn Thr Leu Leu Val Pro
385                 390                 395                 400

Ser Leu Lys Arg Gly Val Ile Phe Arg Ile Lys Leu Asp Pro Thr Tyr
                405                 410                 415

Asn Thr Thr Tyr Asp Asp Ala Val Pro Met Phe Lys Ser Asn Asn Arg
            420                 425                 430

Tyr Arg Asp Val Ile Ala Ser Pro Asp Gly Asn Val Leu Tyr Val Leu
435                 440                 445
```

```
Thr Asp Thr Ser Gly Asn Val Gln Lys Asp Asp Gly Ser Val Thr Asn
    450                 455                 460

Thr Leu Glu Asn Pro Gly Ser Leu Ile Arg Phe Thr Tyr Lys Ala Gln
465                 470                 475                 480
```

<210> SEQ ID NO 25
<211> LENGTH: 1443
<212> TYPE: DNA
<213> ORGANISM: Acinetobacter sp.

<400> SEQUENCE: 25

```
atgaataaac atttattggc taaaattact ttattaggtg ctgctcagct agttacgctc      60
aattcagcat ttgctgatgt ccctcttact ccatctcaat ttgctaaagc gaaaacagaa     120
agctttgaca agaagttct tatatctaat ttaaataagc cacatgcttt gttgtggggg      180
cctgataatc aaatttggtt aacggagcgg gcaacaggta agattctaag agttaatcca     240
gagtcgggca gtgtaaaaac agttttcag gttcctgaga ttgtaaatga tgctgatgga      300
caaaacggtt tattgggttt tgcctttcat cctgacttta aaataatcc ttatatctat      360
gtttcaggta catttaaaaa tccgaaatct acagataaag aattaccgaa tcaaactatt     420
atccgtcgat atacctataa caaagcaaca gatactcttg agaaaccagt agatttattg     480
gcaggattac cttcatcgaa agaccatcag tcgggtcgcc ttgtcattgg tccagaccaa     540
aagatttact atacgattgg tgatcaggga cgtaaccagc ttgcttattt attcttacca     600
aatcaggcac aacatacgcc gactcaacag gaactgagcg aaaagacta tcatacctat      660
atgggtaaag tattacgctt aaatctggat ggaagtattc caaaagataa tccaagcttt     720
aacggtgtaa ttagtcatat ttatacgctc ggtcatcgta atccacaggg cttggcattt     780
actccaaatg gtaaactgtt gcaatctgaa caaggtccaa actctgatga tgaaattaat     840
ctcattgtta aaggtggcaa ctatggctgg ccaaatgtag cgggttataa agatgacagt     900
ggttatgcct atgcaaatta ttcggcagca accataagt cacaaattaa agatttaggg      960
caaaatggag taaagtagc ggcaggtgta cctgtgatga agagtctga atggactggt      1020
aaaaactttg taccgccgtt aaaaacttta tatccgtcc aagatacta taactataat       1080
gacccaacct gtggggatat gacctacatt tgctggccaa cagttgcacc gtcatctgct     1140
tatgtctata agggcggcaa aaaagcaatt tctggttggg aaaatacatt attggttcca     1200
tcttaaaagc gtggtgttat tttccgtatt aagctagatc caacttacag tgctacttat     1260
gatgatgctg tgccgatgtt taagagcaac aatcgttatc gtgacgtgat tgcaagtcca     1320
gatgggaatg ttttatatgt attgactgat acttccggaa atgtccaaaa agatgatggt     1380
tctgtaacga atacattaga aaatccagga tctctgatta gatttacata taagctcag     1440
taa                                                                  1443
```

<210> SEQ ID NO 26
<211> LENGTH: 480
<212> TYPE: PRT
<213> ORGANISM: Acinetobacter sp.

<400> SEQUENCE: 26

```
Met Asn Lys His Leu Leu Ala Lys Ile Thr Leu Leu Gly Ala Ala Gln
1               5                   10                  15

Leu Val Thr Leu Asn Ser Ala Phe Ala Asp Val Pro Leu Thr Pro Ser
            20                  25                  30

Gln Phe Ala Lys Ala Lys Thr Glu Ser Phe Asp Lys Lys Val Leu Ile
```

-continued

```
                35                  40                  45
Ser Asn Leu Asn Lys Pro His Ala Leu Leu Trp Gly Pro Asp Asn Gln
 50                  55                  60

Ile Trp Leu Thr Glu Arg Ala Thr Gly Lys Ile Leu Arg Val Asn Pro
 65                  70                  75                  80

Glu Ser Gly Ser Val Lys Thr Val Phe Gln Val Pro Glu Ile Val Asn
                 85                  90                  95

Asp Ala Asp Gly Gln Asn Gly Leu Leu Gly Phe Ala Phe His Pro Asp
                100                 105                 110

Phe Lys Asn Asn Pro Tyr Ile Tyr Val Ser Gly Thr Phe Lys Asn Pro
                115                 120                 125

Lys Ser Thr Asp Lys Glu Leu Pro Asn Gln Thr Ile Ile Arg Arg Tyr
130                 135                 140

Thr Tyr Asn Lys Ala Thr Asp Thr Leu Glu Lys Pro Val Asp Leu Leu
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
                180                 185                 190

Gln Leu Ala Tyr Leu Phe Leu Pro Asn Gln Ala Gln His Thr Pro Thr
                195                 200                 205

Gln Gln Glu Leu Ser Gly Lys Asp Tyr His Thr Tyr Met Gly Lys Val
                210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
                245                 250                 255

Gly Leu Ala Phe Thr Pro Asn Gly Lys Leu Leu Gln Ser Glu Gln Gly
                260                 265                 270

Pro Asn Ser Asp Asp Glu Ile Asn Leu Ile Val Lys Gly Gly Asn Tyr
                275                 280                 285

Gly Trp Pro Asn Val Ala Gly Tyr Lys Asp Asp Ser Gly Tyr Ala Tyr
290                 295                 300

Ala Asn Tyr Ser Ala Ala Thr Asn Lys Ser Gln Ile Lys Asp Leu Gly
305                 310                 315                 320

Gln Asn Gly Val Lys Val Ala Ala Gly Val Pro Val Met Lys Glu Ser
                325                 330                 335

Glu Trp Thr Gly Lys Asn Phe Val Pro Pro Leu Lys Thr Leu Tyr Thr
                340                 345                 350

Val Gln Asp Thr Tyr Asn Tyr Asn Asp Pro Thr Cys Gly Asp Met Thr
                355                 360                 365

Tyr Ile Cys Trp Pro Thr Val Ala Pro Ser Ser Ala Tyr Val Tyr Lys
370                 375                 380

Gly Gly Lys Lys Ala Ile Ser Gly Trp Glu Asn Thr Leu Leu Val Pro
385                 390                 395                 400

Ser Leu Lys Arg Gly Val Ile Phe Arg Ile Lys Leu Asp Pro Thr Tyr
                405                 410                 415

Ser Ala Thr Tyr Asp Asp Ala Val Pro Met Phe Lys Ser Asn Asn Arg
                420                 425                 430

Tyr Arg Asp Val Ile Ala Ser Pro Asp Gly Asn Val Leu Tyr Val Leu
                435                 440                 445

Thr Asp Thr Ser Gly Asn Val Gln Lys Asp Asp Gly Ser Val Thr Asn
450                 455                 460
```

Thr Leu Glu Asn Pro Gly Ser Leu Ile Arg Phe Thr Tyr Lys Ala Gln
465                 470                 475                 480

<210> SEQ ID NO 27
<211> LENGTH: 1443
<212> TYPE: DNA
<213> ORGANISM: Acinetobacter sp.

<400> SEQUENCE: 27

| | | | | | |
|---|---|---|---|---|---|
| atgaataaac | atttattggc | taaaattact | ttattaggtg | ctgctcagct | acttacgttc | 60 |
| aattcagcat | ttgctgatgt | ccctcttact | ccatctcaat | ttgctaaagc | gaaaacggaa | 120 |
| agctttgata | agaaagttct | tctatctaat | ttaaataagc | cacatgcttt | gttgtgggga | 180 |
| gctgataatc | aaatttggtt | aacggagcgg | caacaggta | agattctaag | agtgaatcca | 240 |
| gagtcgggca | gtgtaaaaac | agtttttcag | gttcctgaga | ttgtaaatga | tgctgatgga | 300 |
| caaaacggtt | tattgggttt | tgcctttcat | cctgacttta | aaataatcc | ttatatctat | 360 |
| gtttcaggta | catttaaaaa | tccgaaatct | acagataaag | aattaccgaa | tcaaactatt | 420 |
| atccgtcgat | atacctataa | caaggcaaca | gataccttg | agaaaccagt | agatttattg | 480 |
| gcaggattac | cttcatcgaa | agaccatcag | tcgggtcgcc | ttgtcattgg | tccagaccaa | 540 |
| aaaatttact | atacgattgg | tgatcagggg | cgtaaccagc | ttgcttattt | attcttgcca | 600 |
| aatcaagcac | agcatacgcc | gactcaacag | gaactgagcg | gcaaagacta | tcatacctat | 660 |
| atgggtaaag | tattacgctt | aaatctggat | ggaagtattc | caaagataa | tccaagcttt | 720 |
| aacggcgtaa | ttagtcatat | ttatacgctc | ggtcatcgaa | acccacaggg | cttggcattt | 780 |
| actccaaatg | gtaaactgtt | gcaatctgaa | cagggtccaa | actctgacga | tgaaattaat | 840 |
| ctcattgtta | aggtggtaa | ctatggctgg | ccaaatgtag | cgggttataa | agatgacagt | 900 |
| ggttatgcct | atgcaaatta | ttcggcagca | accaataagt | cacaaattaa | agatttaggg | 960 |
| caaaatggag | taaaagtagc | ggcaggtgta | cctgtgatga | agagtctga | atggagtggt | 1020 |
| aaaaactttg | taccgccgtt | aaaaacttta | taccgtcc | aaggtaccta | aactataat | 1080 |
| gacccaacct | gtggggatat | gacctacatt | tgctggccaa | cggttgcgcc | gtcatctgct | 1140 |
| tatgtctata | agggaggcaa | aaaagcaatt | tctggttggg | aaaataccctt | actggttcca | 1200 |
| tctttaaagc | gcggtgttat | tttccgtatt | aagctagatc | caacttacag | tgctacttat | 1260 |
| gatgatgcgg | tgccgatgtt | taagagcaac | aatcgttatc | gtgacgtgat | tgcaagtcca | 1320 |
| gatgggaatg | ttttatatgt | attgactgat | acttccggaa | atgtccaaaa | agatgatggt | 1380 |
| tctgtaacga | atacattaga | aaacccagga | tctctgatta | gatttacata | taaagctcag | 1440 |
| taa | | | | | | 1443 |

<210> SEQ ID NO 28
<211> LENGTH: 480
<212> TYPE: PRT
<213> ORGANISM: Acinetobacter sp.

<400> SEQUENCE: 28

Met Asn Lys His Leu Leu Ala Lys Ile Thr Leu Leu Gly Ala Ala Gln
1               5                   10                  15

Leu Leu Thr Phe Asn Ser Ala Phe Ala Asp Val Pro Leu Thr Pro Ser
                20                  25                  30

Gln Phe Ala Lys Ala Lys Thr Glu Ser Phe Asp Lys Lys Val Leu Leu
            35                  40                  45

-continued

```
Ser Asn Leu Asn Lys Pro His Ala Leu Leu Trp Gly Ala Asp Asn Gln
 50              55                  60

Ile Trp Leu Thr Glu Arg Ala Thr Gly Lys Ile Leu Arg Val Asn Pro
 65                  70                  75                  80

Glu Ser Gly Ser Val Lys Thr Val Phe Gln Val Pro Glu Ile Val Asn
                     85                  90                  95

Asp Ala Asp Gly Gln Asn Gly Leu Leu Gly Phe Ala Phe His Pro Asp
                100                 105                 110

Phe Lys Asn Asn Pro Tyr Ile Tyr Val Ser Gly Thr Phe Lys Asn Pro
                115                 120                 125

Lys Ser Thr Asp Lys Glu Leu Pro Asn Gln Thr Ile Ile Arg Arg Tyr
                130                 135                 140

Thr Tyr Asn Lys Ala Thr Asp Thr Leu Glu Lys Pro Val Asp Leu Leu
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
                180                 185                 190

Gln Leu Ala Tyr Leu Phe Leu Pro Asn Gln Ala Gln His Thr Pro Thr
                195                 200                 205

Gln Gln Glu Leu Ser Gly Lys Asp Tyr His Thr Tyr Met Gly Lys Val
                210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
                245                 250                 255

Gly Leu Ala Phe Thr Pro Asn Gly Lys Leu Leu Gln Ser Glu Gln Gly
                260                 265                 270

Pro Asn Ser Asp Asp Glu Ile Asn Leu Ile Val Lys Gly Gly Asn Tyr
                275                 280                 285

Gly Trp Pro Asn Val Ala Gly Tyr Lys Asp Asp Ser Gly Tyr Ala Tyr
                290                 295                 300

Ala Asn Tyr Ser Ala Ala Thr Asn Lys Ser Gln Ile Lys Asp Leu Gly
305                 310                 315                 320

Gln Asn Gly Val Lys Val Ala Ala Gly Val Pro Val Met Lys Glu Ser
                325                 330                 335

Glu Trp Ser Gly Lys Asn Phe Val Pro Pro Leu Lys Thr Leu Tyr Thr
                340                 345                 350

Val Gln Gly Thr Tyr Asn Tyr Asn Asp Pro Thr Cys Gly Asp Met Thr
                355                 360                 365

Tyr Ile Cys Trp Pro Thr Val Ala Pro Ser Ser Ala Tyr Val Tyr Lys
                370                 375                 380

Gly Gly Lys Lys Ala Ile Ser Gly Trp Glu Asn Thr Leu Leu Val Pro
385                 390                 395                 400

Ser Leu Lys Arg Gly Val Ile Phe Arg Ile Lys Leu Asp Pro Thr Tyr
                405                 410                 415

Ser Ala Thr Tyr Asp Asp Ala Val Pro Met Phe Lys Ser Asn Asn Arg
                420                 425                 430

Tyr Arg Asp Val Ile Ala Ser Pro Asp Gly Asn Val Leu Tyr Val Leu
                435                 440                 445
```

```
Thr Asp Thr Ser Gly Asn Val Gln Lys Asp Asp Gly Ser Val Thr Asn
    450             455             460

Thr Leu Glu Asn Pro Gly Ser Leu Ile Arg Phe Thr Tyr Lys Ala Gln
465             470             475             480
```

GLUCOSE DEHYDROGENASE AND PRODUCTION THEREOF

This application is a 371 of PCT/EP2004/004412, filed Apr. 27, 2004, which claims foreign priority benefit under 35 U.S.C. §119 of the German Patent Application No. 10 320 259.5 filed May 7, 2003.

The invention relates to novel PQQ-dependent soluble glucose dehydrogenases (sPQQGDH) from *Acinetobacter* and to a process for their preparation by overexpression in suitable microbial expression systems.

Patients suffering from diabetes must measure their blood glucose regularly. Measurement of glucose likewise plays an important part in fermentation processes. In many cases, glucose is determined enzymatically. For this purpose, either glucose oxidase, or, in rare cases, also glucose-6-phosphate dehydrogenase are employed. The methods based on glucose oxidase have the disadvantage that the enzyme transfers the electrons not just to the added mediators but also to the oxygen present. The result of the measurement is therefore dependent on the oxygen partial pressure. Efforts have been made for some time to replace the present enzymes by sPQQ-dependent glucose dehydrogenases. PQQ stands for pyrroloquinoline quinone. PQQ is the prosthetic group of glucose dehydrogenase (GDH). It transfers redox equivalents. The advantage of these enzymes is that the measurement is independent of the oxygen partial pressure and a more accurate measurement is possible. In addition, measurement in smaller sample volumes is possible through use of these enzymes.

Two different PQQGDHs are to be found in the literature. One form is membrane-bound (mPQQGDH) and is unsuitable for use in glucose sensors. The other form is soluble (sPQQGDH) and has been found variously in strains of the genus *Acinetobacter* (Biosci. Biotech. Biochem. 59 (8), pp. 1548-1555, 1995). The enzyme is a homodimer and has a molecular weight of 50 kDa. The soluble and the membrane-bound PQQGDH have no sequence homology and are different immunologically and in terms of their kinetics (Cleton-Jansen et al., 172 (11), pp. 6308-6315, J. Bacteriol. 1990) (Matsushita et al., Biochemistry 28 (15), pp. 6276-6280, 1989).

The sPQQGDH from *Acinetobacter* has been known for some time. All authors use the strains LMD 79.41 (Kojima et al., Biotechnology Letters, 22, pp. 1343-1347, 2000), NCIMB 11517 or JCM 6841 (both: US 2001021523).

The DNA sequences of the sPQQGDH of these strains are deposited in the Genbank under the access numbers X15871 (LMD 79.41), E28183 (JCM 6841) and E28182 (NCIMB 11517).

Many attempts have been made to alter the properties of these sPQQGDH by modifying the gene sequences. (EP 1 167 519 A1, EP 1 176 202 A1, Sode und Kojima, Biotech. Letters, Vol. 19, (11) pp. 1073-1077, 1997). The aim in these cases was to improve the substrate specificity and the thermal stability of the enzyme. EP 1 167 519 A1 describes the replacement of individual amino acids of the sPQQGDH from *Acinetobacter* LMD 79.41 in order to obtain increased thermal stability. Alterations are made in amino acids 209, 210, 231, 420 and 421. WO 02/072839 A1 describes further alterations in the amino acid sequence in order to achieve increased thermal stabilities and improvements in the water solubility. Replacements were made in positions 167, 231, 340, 415 and 418. The numbering is based in both cases on that used in EP 1 167 519. When comparing the enzyme from *Acinetobacter* LMD 79.41 with the novel sPQQGDH according to the invention and that from *Acinetobacter* JCM 6841 it is necessary also to take account of the fact that the two last-mentioned enzymes are two amino acids longer than that from LMD 79.41. The mature enzyme and the signal peptide are considered in this connection.

WO 02/34919 A1 describes replacement of individual amino acids with the aim of reducing the affinity of the enzyme for maltose. The thermal stability of the enzyme is unaffected.

Enzymes are normally prepared by heterologous expression thereof in *E. coli*. The problem arising on expression of sPQQGDH is that although *E. coli* can synthesise the enzyme, it cannot synthesise cofactor PQQ. Although, according to Sode et al. (J. Biotechnology, 49, 239-243, 1996) expression of the apoenzyme mPQQGDH is possible in the case of the membrane-bound glucose dehydrogenase, it is unstable and is broken down again during culturing of the cells. Matsushita et al. (Biosci. Biotechnol. Biochem. 59, 1548-1555, 1995) postulate a conformational change in the enzyme occurring on binding of the cofactor and protecting the holoenzyme from tryptic digestion.

For this reason, all research groups and manufacturers have made efforts to prepare active and stable enzyme in such a way that either PQQ is added during culturing of the cells, or the expression takes place in strains themselves able to form PQQ. Sode et al. (J. Biotechnology, 49, 239-243, 1996) succeeded in coexpressing mPQQGDH together with the genes for PQQ synthesis in *E. coli* and achieved about 1500 U/I at an OD of 4. Addition of PQQ during culturing of the cells achieves 1100 U/I. However, the system has the problem that the cells do not reach high optical densities and die during enzyme production (Kojima et al., Biotechnology Letters, 22, 1343-1347, 2000). The authors in the previously cited publication describe the synthesis of active sPQQGDH in *Klebsiella pneumoniae*. This organism is genetically available and has the ability to synthesize PQQ. In this case, therefore, activities of about 14 000 U/I are reached, although additional PQQ feeding is necessary. Yoshida et al. (Enzym. Microb. Technol. 30, pp. 312-318, 2002) expressed soluble sPQQGDH in *Pichia pastoris* heterologously and thus achieved usable enzyme yields of up to 200 000 U/I. However, it is necessary for this purpose to reach very high cell densities. In addition, the enzyme is glycosylated and must additionally be purified by a precipitation and two ion exchanges. Cost-effective preparation is impeded in particular by the elaborate purification and the glycosylation.

The Toyobo Co. Ltd., Japan, describes in JP 09140378 the preparation of sPQQGDH using *Acinetobacter calcoaceticus*. 60 U/I are reached after three purification steps. In order to increase the productivity of the system, the enzyme was subsequently expressed heterologously in *Pseudomonas putida*, because this strain is able to synthesize PQQ.

Olsthoorn and Duine (Arch. Biochem. Biophys. 336 (1), 42-48, 1996) describe the batch culturing of an *E. coli* clone which expresses sPQQGDH in a 100 l fermenter. After the culturing, the enzyme is purified by three column steps. The clone forms no PQQ; the cofactor is added only in the enzyme assay. The yields amount to 10 mg of pure protein per 1 of grown culture. The low cell density of the culture, the elaborate purification process and the yield, however, make the process appear uneconomic.

DESCRIPTION OF THE INVENTION

During a screening, 12 strains of the species *Acinetobacter calcoaceticus* which form an sPQQGDH were found. Typing of the novel strains by the Deutsche Sammlung von Mikroorganismen und Zellkulturen (DSMZ) revealed 99.8% homology of the partial 16S rDNA sequence to the *Acineto-* bacter calcoaceticus type strain. However, the observed utilization of L-malate and the inability to break down L-phenylacetate is unusual for the type strain This property is shown by all 12 strains found.

The sPQQGDHs formed by these strains differ from the previously known enzymes in substantial properties. On the one hand, they have a thermal stability which is improved by comparison with the enzyme from the type strain (see Example 3). The nucleotide sequences and the sequence of the amino acids are likewise different.

BRIEF DESCRIPTION OF THE DRAWING

FIG. 1 shows the amino acid sequence of the newly found soluble pyrroloquinoline quinone glucose dehydrogenases (sPQQGDH) compared with Acinetobacter LMD 79.41 and JCM 6841.

Figures 1A, 1B:
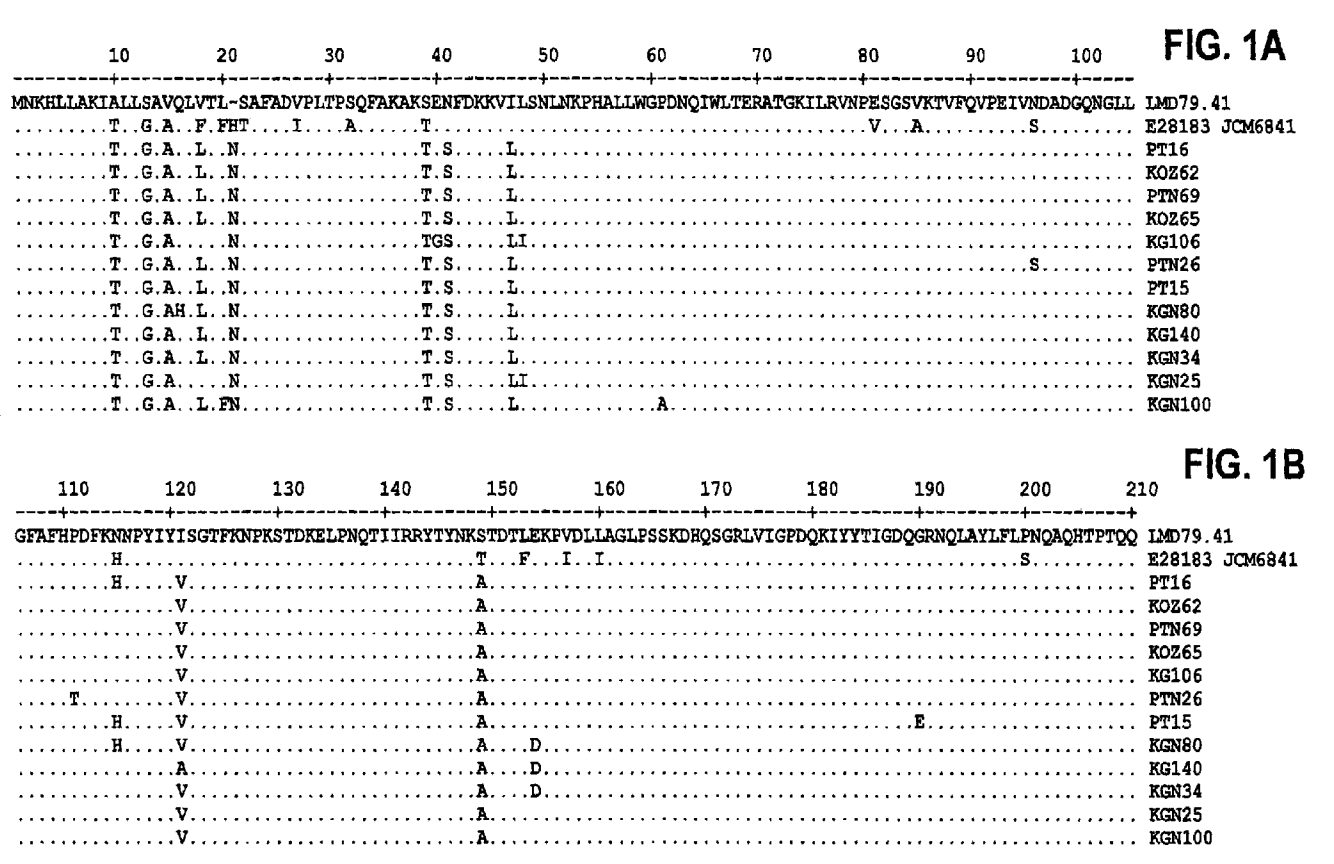
Figures 1C, 1D:
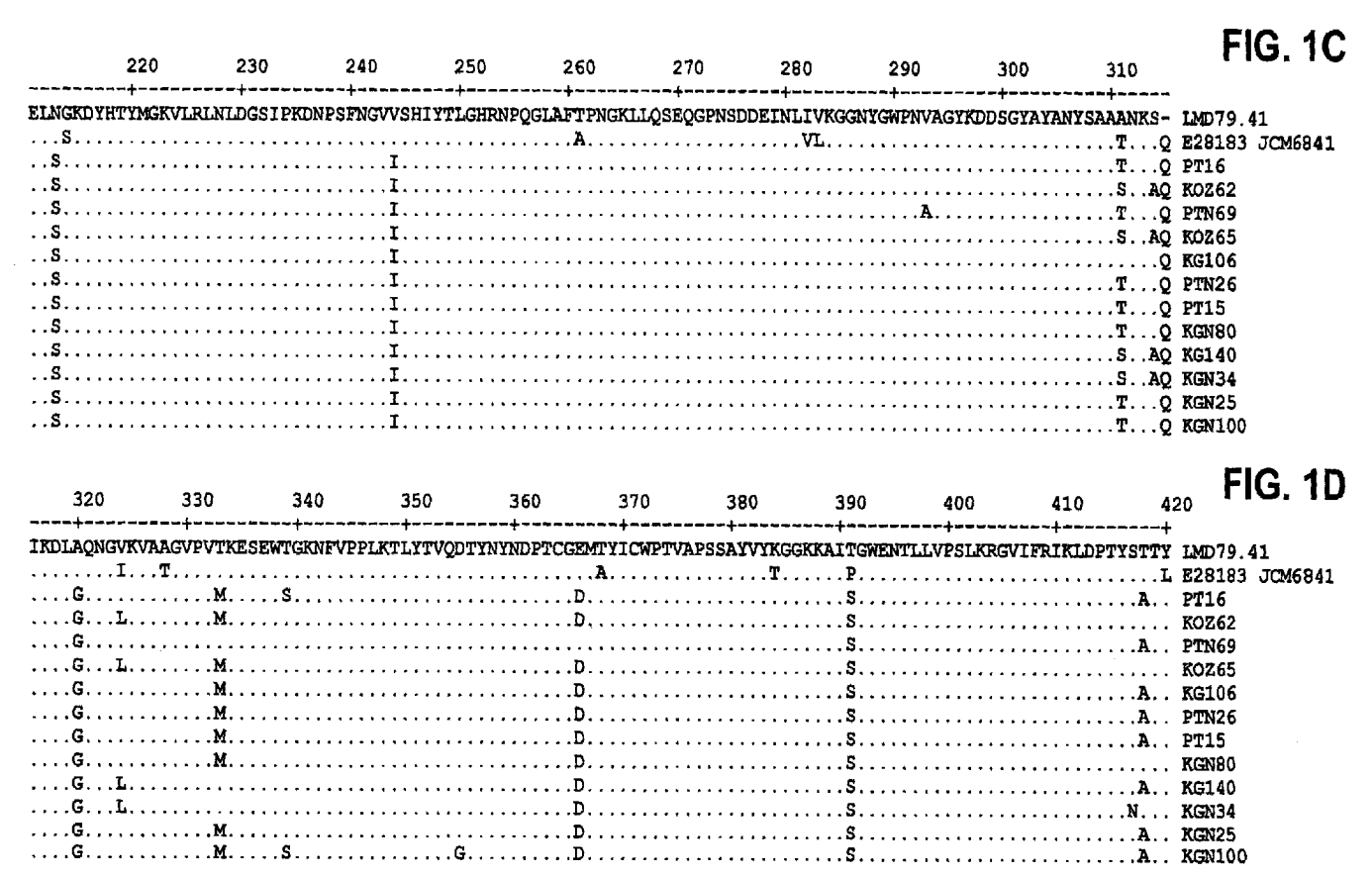

The assignment of SEQ ID NOs to the sPQQGDHs of FIG. 1 is given in Table 3 below.

Table 3: Assignment of SEQ ID NOs to the reference IDs of the pyrroloquinoline quinone glucose dehydrogenases of FIG. 1

TABLE 3

Assignment of SEQ ID NOs to the reference IDs of the pyrroloquinoline quinone glucose dehydrogenase of FIG. 1

| Reference ID | SEQ ID NO | TYPE |
| --- | --- | --- |
| LMD79.41 | 1 | DNA |
| LMD79.41 | 2 | PRT |
| E28183 JCM6841 | 3 | DNA |
| E28183 JCM6841 | 4 | PRT |
| PT16 | 5 | DNA |
| PT16 | 6 | PRT |
| KOZ62 | 7 | DNA |
| KOZ62 | 8 | PRT |
| PTN69 | 9 | DNA |
| PTN69 | 10 | PRT |
| KOZ65 | 11 | DNA |
| KOZ65 | 12 | PRT |
| KG106 | 13 | DNA |
| KG106 | 14 | PRT |
| PTN26 | 15 | DNA |
| PTN26 | 16 | PRT |
| PT15 | 17 | DNA |
| PT15 | 18 | PRT |
| KGN80 | 19 | DNA |
| KGN80 | 20 | PRT |
| KG140 | 21 | DNA |
| KG140 | 22 | PRT |
| KGN34 | 23 | DNA |
| KGN34 | 24 | PRT |
| KGN25 | 25 | DNA |
| KGN25 | 26 | PRT |
| KGN100 | 27 | DNA |
| KGN100 | 28 | PRT |

Sequence analysis of the 12 genes which code for the novel sPQQGDHs revealed the following results (see FIG. 1):

The nucleotide sequences of all the newly found sPQQGDHs differ distinctly from those of the enzymes from Acinetobacter LMD 79.41 and Acinetobacter JCM 6841 and NCIMB 11517.

The amino acid sequences which can be derived from the respective nucleotide sequences likewise differ from the previously known sequences. The sPQQGDH from Acinetobacter LMD 79.41 has 478 amino acids, including the signal peptide, while those from the two other known strains Acinetobacter JCM 6841 and Acinetobacter NCIMB 11517, and those from the sequences found here each have 480 amino acids, including signal peptide.

The amino acid sequences of the newly found sPQQGDHs differ in numerous positions from those previously known. Surprisingly, an amino acid different from that in all previously described enzymes was found at 12 positions with all the genes newly described herein. In addition, at least 75% of the genes newly described herein have an amino acid different from that in the previously described genes at four positions. Moreover, in the enzymes newly described herein there are further exchanges, which occur singly or in some of the enzymes.

The specific replacements in the newly found sPQQGDH according to the invention are of the following amino acids. The numbering of amino acids is based on the numbering in the enzyme from the strain Acinetobacter JCM 6841, which comprises 480 amino acids, including signal peptide (see FIG. 1):

All the sPQQGDHs which have at positions 21 an N and 41 an S and 47 an L and 121 a V or an A and 149 an A and 213 an S and 244 an I and 320 a G and 391 an S and 452 an S and 474 an R and 480 a Q as amino acid are according to the invention.

Further according to the invention are all the sPQQGDHs in which the following exchanges may occur in addition to the exchanges described above:

There may be at positions 16 an H, at 18 an L, at 20 an F, at 40 a G, at 48 an I, at 61 an A, at 111 a T, at 154 a D, at 190 a D, at 293 an A, at 311 an S, at 314 an A, at 324 an L, at 333 an M, at 339 an S, at 355 a G, at 366 a D, at 417 an N and at 418 an A.

It has surprisingly been found that the newly found enzymes are all more thermally stable than the wild-type enzyme. The thermal stability is an essential criterion for successful use of sPQQGDH as glucose sensor. Thus, the remaining activities found on incubation at 60° C. and 70° C. for one hour were all higher than with the enzyme from Acinetobacter LMD 79.41. The remaining activity found at 60° C. with the sPQQGDHs according to the invention were between 51.5% and 12.5%. The wild type showed only 1.8% of its original activity in an identical approach. Between 26.7% and 8.8% of the initial activity were observed at 70° C., whereas the wild-type enzyme had only 6.4% of the original activity.

Various attempts have been made in the past to increase the thermal stability of sPQQGDH by targeted and random exchange of amino acids.

However, EP 1 167 519 A1 claims the exchange of amino acids at positions markedly different from those in the sPQQGDHs according to the invention. The same applies to the exchanges described in WO 02/072839. This likewise applies to the exchanges described in WO 02/34919 A1. The increased thermal stability of the sPQQGDHs according to the invention thus correlates with the exchange of a whole group of amino acids whose influence on this property was not previously known.

The enzymes according to the invention can be prepared by cultivating the relevant strain in a suitable medium. It is possible to use for this purpose the media described in the literature, such as nutrient broth (Difco 0003). After the cells have grown, they are harvested and disrupted. The enzyme is purified as described below.

The sPQQGDHs from the wild type are preferably cloned into a suitable host. Possibilities therefor are the usual genetically readily available prokaryotes such as members of the genus Bacillus, Klebsiella, Pseudomonas, and E. coli. The enyzmes may furthermore also be expressed in eukaryotes such as members of the genera Pichia, Saccharomyces, Hansenula, Aspergillus or Kluyveromyces. The enzymes may also be expressed in plants or animal cell lines.

It is possible to employ for the cloning standard methods such as PCR with degenerate primers or hybridization of genomic libraries with suitable probes. Expression is preferably carried out in E. coli. The expression is normally carried out in the strains BL21, DH5, HB101, JM101, RV308, TOPP, TOP10, XL-1 and derivatives thereof. The strains W3110 and DH5 are preferably used. Conventional expression vectors can be employed for this purpose. The vectors typically comprise an origin of replication, an antibiotic resistance and a promoter sequence. Examples of vectors which can be employed are the following: pUC18/19, pBluescript, pTZ, pGEX, pPROEx, pcDNA3.1, YEp24, pBAC, pPICZ. Vectors of the pMAL, pET, pTrx, pCAL, pQE and pPROTet series are preferred. Expression vectors of the pASK-IBA 2 to pASK-IBA 7 series are particularly preferably employed. Usual antibiotics for resistance selection are, for example, ampicillin, kanamycin, tetracycline and chloramphenicol.

It is also possible to use expression systems which lead to the protein being secreted into the medium.

The vectors can be transferred to the host cell by conventional methods. Examples employed for this purpose are: electroporation, protoplast fusion, chemical transformation.

Synthesis of the cloned sPQQGDHs is induced by adding an inducer. The inducers employed for this purpose are those suitable for the chosen expression system, such as, for example. IPTG, tryptophan, glucose and lactose. The inducer anhydrotetracycline is particularly preferably used.

The recombinant cell lines are cultured in media suitable therefor. Conventional processes used for culturing prokaryotes and eukaryotes are suitable for this purpose. The culturing can be carried out in suitable fermenters. The organisms are preferably cultivated in such a way that very high cell densities are reached. To do this it is necessary for the feeding with a C source and an N source to be suitably controlled by a strategy such that no toxic metabolic products result (for overview: Schügerl et al. (editors) in: Bioreaction Engineering, pp. 374-390, Springer-Verlag, Berlin, 2000; Yee and Blanch, Bio/Technology, 10 (2), pp. 1550-1556, 1992).

A process suitable for the purposes of this invention is for example that of Riesenberg et al., Appl. Microbiol. Biotechnol, 34, pp. 77-82, 1990.

Whereas the cultivation of the cells ideally takes place at 28-37° C., the temperature is lowered to 10-28° C. for expression of the protein. It is preferably at 15-25° C. and particularly preferably at 20-22° C.

It has surprisingly been found that on use of the process according to the invention distinctly higher yields of active enzyme are attained than previously described in the literature. When an E. coli clone is cultured in a batch culture it is possible in this way to obtain up to 48 mg of pure protein from one litre of culture supernatant (see Examples 5 and 6). Yoshida et al. (Enzym. Microbiol. Technol., 30, pp. 312-318, 2002) attained 43 mg/l. However, elaborate purification of the enzyme is necessary, and it is glycosylated. Olsthoorne and Duine (Arch. Biochem. Biophys. 336 (1), pp. 42-48, 1996, report a yield of 10 mg/l.

If the cells having the enzymes according to the invention are cultured in fermentation with high cell density, it is in fact possible to reach more than 220 mg of pure enzyme per 1 of culture liquid (Example 8).

Culturing of the cells is followed by harvesting and disruption thereof by suitable methods such as, for example, French press, addition of detergents or ultrasound. The protein solution is buffered and brought to a slightly alkaline pH. The buffer is adjusted to a pH between 7 and 9, and is preferably between 7.8 and 8.2.

Buffer substances which can be employed are the buffers customary in biochemistry, such as Tris, MOPS or PIPES buffers, potassium phosphate buffer; the concentration ought to be 5-100 mM, and is preferably in a range of 20-70 mM and particularly preferably 50 mM.

The sPQQGDH can now be purified very easily from the protein solution. To do this, the protein solution is either purified by a conventional ion exchange chromatography, or the ion exchange material is directly added to the protein solution and then separated from the remainder of the liquid on a suction funnel. Suitable ion exchangers are cation exchangers such as, for example, Lewatit resins CM-, S—, SM-Sepharose, CM-, SP-Sephadex, Amberlyst 15, Amberlite CG-50, Amberlite IR-120, carboxymethyl-, sulphoxyethyl-, oxycellulose, cellulose phosphate and CM-Toyopearl. CM-Toyopearl is preferably employed.

The protein is then eluted from the ion exchange material by conventional methods. An increasing NaCl gradient is employed for this, and the buffer used is that also employed previously for binding the protein to the ion exchange material. The enzyme is normally eluted at a concentration of about 200 mM NaCl.

The enzyme can then be purified further, and it is likewise possible to reduce the salt content by conventional methods such as dialysis and ultrafiltration.

The preparation and purification of the sPQQGDH according to the invention preferably takes place as apoenzyme, and the cofactor PQQ is added only when the enzyme has been completely purified. Addition of the PQQ ideally takes place in conjunction with changing the buffer of the enzyme after purification on the ion exchanger.

The PQQ can be added before the buffer is changed or thereafter. It is preferably added beforehand. The amount depends on the content of the protein solution. From 0.1 to 5 mol of PQQ can be added per mole of active enzyme. It is ideal to add from 0.5 to 2 mol, particularly preferably 2 mol, of PQQ per mole of active protein. However, it is also possible for the enzyme to be prepared and purified as holoenzyme. For this purpose the PQQ can be added during cell culturing, during cell disruption or prior to purification. A further possibility is for the sPQQGDHs according to the invention also be prepared as holoenzymes by heterologous expression thereof in organisms able to synthesise PQQ. These may be for example organisms from the genus *Klebsiella* or *Pseudomonas*.

The novel sPQQGDHs are employed according to the invention for glucose measurement. They are particularly preferably employed in instruments which can be used to measure blood glucose. It is also possible in addition to employ the enzymes for glucose measurement for example in fermentation processes.

If the sPQQGDHs according to the invention are employed for diagnostic purposes, such a test kit typically includes a buffer, a mediator and some units of enzymic activity. 0.5-10 U are typically employed, and 1-5 U are preferably employed. Various formulations of the enzyme are possible for this purpose. It can for example be freeze- or spray-dried and formulated as solution. Suitable electrodes may be carbon, gold or platinum electrodes. The enzyme is normally immobilized on the electrode. Crosslinking agents are normally used for this purpose but the enzyme can also be encapsulated. Further possibilities for immobilizing it are by means of a dialysis membrane, by photocrosslinking, electrically conducting or redox polymers. Combinations of the abovementioned methods are also possible.

The enzymes are preferably applied as holoenzymes but they can also be employed as apoenzymes, in which case the necessary PQQ is supplied in a second layer. The novel sPQQGDHs are preferably immobilized on a carbon electrode with glutaraldehyde and then treated with a reagent containing amines for complete reaction of excess glutaraldehyde.

EXAMPLES

Example 1

Search for Novel Strains Which Produce sPQQGDH

Soil samples were suspended in saline (0.9% NaCl), and aliquots were streaked onto agar plates which contained a nutrient medium with gluconate as sole carbon source. The medium had the following composition:

| | |
|---|---|
| NaCl | 5 g |
| $MgSO_4$ | 0.2 g |
| $NH_4H_2PO_4$ | 1 g |
| $K_2HPO_4$ | 1 g |
| Sodium gluconates | 2 g |
| Yeast extract | 0.5 g |
| Agar | 15 g |
| Dist. water | 1000 ml |
| pH | 7.0 |

The plates were incubated at 30° C. for 24-48 hours.

Alternatively, Pseudomonas-Agar from Oxoid was also used. The incubation conditions were identical.

Selected grown colonies were isolated on glucose-eosin-methylene blue agar. This had the following composition:

| | |
|---|---|
| $K_2HPO_4$ | 1 g |
| Glucose | 18 g |
| Peptone | 10 g |
| Eosins | 0.4 g |
| Methylene blue | 0.06 g |
| Agar | 16 g |
| Dist. water. | 1000 ml |
| pH | 7.6 |

The plates were incubated at 30° C. for 24 hours. Positive clones can be identified by being dark red and/or having a green lustre. These colonies are again streaked on nutrient agar (Oxoid) in order to check their purity. The composition thereof was as follows:

| | |
|---|---|
| Meat extract | 1 g |
| Yeast extract | 2 g |
| Peptone | 5 g |
| NaCl | 5 g |
| Agar | 15 g |
| Dist. water | 1000 ml |
| pH | 7.4 |

The plates were incubated at 30° C. for 48 hours and again isolated. The purified strains were subsequently cultured in 100 ml of liquid nutrient broth (Oxoid) at 30° C. for 20 h; the medium had the following composition:

| | |
|---|---|
| Meat extract | 3 g |
| Bakto peptone | 5 g |
| Glucose | 1 g |
| Dist. water | 1000 ml |

Culturing was followed by harvesting of the cultures (4500×g, 40 min, 4° C.) and washing with saline (0.9% NaCl). The pellets were resuspended in 5 ml of 50 mM KP buffer of pH 7.2 and disrupted with ultrasound. The extract was again centrifuged at 10 000×g at 4° C. for 30 min, and the GDH activity in the cell-free supernatant was measured. It was possible to isolate 26 strains with GDH activity on the screening medium with gluconate as sole carbon source. It was possible to isolate four strains after culturing on the Pseudomonas medium.

Example 2

Purification of the Enzymes

The strains whose sPQQGDHs were to be investigated were cultured in 8 l of NB medium (Oxoid), which contained 0.1% glucose at 30° C. for 20 h. The cells were harvested (4500×g, 40 min, 4° C.), washed with 0.9% saline and taken up in 150-200 ml of 10 mM MOPS of pH 8.0. The cells were disrupted with ultrasound. The cell-free extract was loaded onto 300 ml of TSK gel CM-Toyopearl 650M (Tosoh Corp.) and washed with 3-4 column volumes of 10 mM MOPS of pH 8.0. Elution took place with a 0-0.3 M NaCl gradient with a 3-4-fold column volume. Active fractions were pooled, transferred into a dialysis tube and concentrated by addition of high-viscosity carboxylmethylcellulose as water absorber. The concentrated sample was resuspended with 3.5 volume of 10 mM K-MOPS of pH 6.8 and again purified on the CM-Toyopearl column. Equilibration of the column and washing took place with 10 mM K-MOPS of pH 6.8, and elution was carried out with a 0-0.3 M NaCl gradient. The active fractions were pooled and concentrated as described above. They served as starting material for determining the thermal stability.

Example 3

Test of Thermal Stability

The thermal stability was determined by incubating the purified enzymes at 50, 60 and 70° C. for 60 minutes. The incubation took place in 50 mM Pipes at pH 6.5 in the presence of 1 mM $CaCl_2$, 0.1% Triton X-100, 0.1% BSA and 5 µM PQQ. After the incubation, the samples were cooled on ice and the remaining activity was determined. It was expressed as a percentage of the original activity.

TABLE 1

Thermal stability of novel sPQQGDH from various new isolates

| Strain | 50° C. | 60° C. | 70° C. |
|---|---|---|---|
| KGN25 | 100 | 14.3 | 13.1 |
| KGN34 | 104.2 | 19.8 | 14.6 |
| KGN80 | 94.3 | 22.6 | 18.9 |
| KGN100 | 95.9 | 12.5 | 13.5 |
| KG106 | 102.6 | 33.4 | 13.9 |
| KG140 | 105.5 | 20.5 | 8.8 |
| KOZ62 | 107.7 | 42.8 | 14.7 |
| KOZ65 | 103.8 | 34.6 | 19.2 |
| PT15 | 100.0 | 25.4 | 16.3 |
| PT16 | 85.0 | 51.5 | 14.9 |
| PTN26 | 120.7 | 27.5 | 22.4 |
| PTN69 | 93.2 | 36.4 | 26.7 |
| LMD79.41 wild type | 95.6 | 1.8 | 6.4 |

Example 4

Cloning and Analysis of the Novel sPQQGDH Genes

For cloning the sPQQGDH genes from the novel strains described here it was initially attempted to amplify the complete coding sequence on genomic DNA with synthetic oligonucleotides in a PCR. The primers which were used for this and were derived from the published sPQQGDH sequence (X15871; LMD 79.41) did not, however, lead to PCR products, because the sequences of the sPQQGDHs according to the invention differ particularly greatly from the wild type in the region of the signal peptide and close to the stop codon. For this reason, various primers from both strands of the wild-type sequence which were intended to lead on use in a PCR to amplification of fragments of the coding sequence were used. It was possible with some of these primer combinations to isolate such fragments from the strains described in Example 3. Commercial kits were used for all the PCR reactions, usually the PCR master kit from Roche, in accordance with the manufacturer's instructions. It was possible with the primers GDH-fwd P1 (5'-CCA GAT AAT CAA ATT TGG TTA AC-3') and GDH-rev P7 (5'-CAT CAC GAT AAC GGT TYT TGC-3') to isolate fragments about 1200 bp in size. The resulting DNA pieces were then sequenced. An inverse PCR was carried out in order to obtain the complete sequence of the individual genes (Sambrook and Russell: Molecluar Cloning—A Laboratory Manual. CSHL Press (2001), p. 8.81). The primers employed for this purpose in the present case were each positioned on the margin of the fragment in such a way that the still unknown part of the GDH gene is synthesized in a further PCR. Such a PCR reaction was carried out on genomic DNA of the respective strain, which had been cut with the restriction endonucleases EcoRI and BglII and then recircularized by T4 ligase. The primers used were GDH-3Mid (5'-GGGATATGACCTACATTTGCTGGC-3') and GDH-5Mid (5'-TGTCCATCAGCRTCATTTACAAYCT-CAG-3'), which initiated directed DNA synthesis respectively in the direction of the 3' end (GDH-3Mid) and 5' end (GDH-5Mid) of the GDH gene. The amplicons obtained in this way contained the as yet missing portions of the coding sequence, as emerged by cloning into the vector pCR2.1 and subsequent sequencing. The DNA sequences which were now completely available were used anew to develop primers which made it possible for the coding sequence from start codon to stop codon to be cloned directly. The primers were chosen in this case so that cloning into the vector pASK-IBA3 is possible in accordance with IBA's instructions. For this purpose, a BsaI cleavage site is positioned directly in front of the coding sequence (in the 5'-binding primer) and one was positioned directly thereafter (in the 3'-binding primer) so that directed ligation of the BsaI-cut PCR product into the BsaI open vector pASK-IBA3 is possible. The 5' primer used was GDH-U3(5'-TGGTAGGTCTCAAATGAATAAACATT-TATTGGCTAAAATTAC-3'), and the 3' primers used were GDH-L3

(5'-ATGGTAGGTCTCAGCGCTCTGAGCTIT-1ATATGTAAACCTAATCAAAG-3'; for the GDH from clone PT15) and GDH-L4

(5'-ATGGTAGGTCTCAGCGCTCTGAGCT-TATATGTAAATCTAATCAGAG-3';

for all other clones). The resulting plasmid as were referred to as pA13-X. Instead of "X", the strain number of the clone from which the genomic DNA was isolated is inserted. For the purposes of comparison, the sPQQGDH gene from the wild-type strain LMD79.41 was cloned in the same way. However, the primers used for this were derived from the published sequence. This plasmid was referred to as pAI3-wt.

The described plasmids were transferred into the *E.coli* strain DH5α (from Invitrogen) by chemical transformation. The bacterial strains obtained in this way were referred to as DH5α::pAI3-X. The plasmids were transferred in a similar way into a further *E.coli* strain, W3110 (ATCC 27325). These strains were then referred to as W3110::pAI3-X.

Example 5

Recombinant Preparation of sPQQGDH with *E. coli*

The preculture was prepared as follows. 0.1 ml of a glycerol stock of DH5α::pAI3-KOZ65 cells was added to 2 ml of LB medium (50 µg/ml ampicillin) and shaken at 37° C. and 225 rpm overnight. For the main culture, 1 l of TB medium (50 µg/ml ampicillin) was inoculated with the fully grown preculture. The culture was shaken at 37° C. and 225 rpm until an OD of about 1 was reached. The main culture was then induced with an anhydrotetracycline (AHT) stock solution. The inducer was dissolved in DMF for this purpose. The final concentration of AHT in the culture was 0.2 µg/ml, and induction took place at 27° C. and 225 rpm for 24 hours. The OD of the main culture was then 4.2.

The cells were harvested by centrifugation of the main culture at 3220×g and 4° C. for 15 min. The cell pellets were resuspended in 40 ml (=1/25 of the total volume) in 75 mM Tris-HCl of pH 8.0, and disrupted using a French press. This is done by treating the complete cell suspension with the French press twice. The lysate, which may be cloudy due to inclusion bodies and cell detritus, was centrifuged at 48 745×g and 4° C. for 10 min. The protein content and the activity of the supernatant were assayed. The protein content was 9.25 mg/ml, and the activity was 1.4 kU/ml. Based on the original culture, 56 kU were obtained per 1 of culture.

Example 6

Purification of the Recombinant sPQQGDH 11.2 ml of the supernatant from Example 5 were separated by chromatography on a cation exchanger (Toyopearl CM-650M, from TOSOH BIOSEP GmbH) at 4° C. An XK 50/20 column (from Amersham Pharmacia Biotech) with a column bed of about 130 ml is used for this purpose; the flow rate was 8 ml/min. The column was equilibrated with 10 column volume of 10 mM K-MOPS of pH 8.0+1 mM $CaCl_2$ after which the sample is loaded. The column was washed with 4 column volume of 10 mM K-MOPS of pH 8.0+1 mM $CaCl_2$, and it was then eluted with a linear salt gradient from 0 to 0.4 N NaCl in 10 mM K-MOPS of pH 8.0 (in each case including 1 mM $CaCl_2$), collecting the eluate in fractions. Regeneration of the column takes place with 3 column volume of 1 N NaCl+1 mM $CaCl_2$.

The eluate fractions were assayed for activity in 96-well microtitre plates with flat base in order to find the active fractions. The colour solution had the following composition:

0.2 mM PMS (phenazine methosulphate in $H_2O$)

+0.22 mM NTB (nitrotetrazolium blue in $H_2O$)

+3 µM PQQ Na salt (in DMSO)

in 20 mM Tris/HCl of pH 7.5 with 2% glucose

The assay was carried out as follows: in each case 90 μl of sample were introduced into a microtitre plate, and 110 μl of colour solution were added to each; the colour reaction can usually be observed after only one minute. On the basis of the results in the online UV chromatogram and in the activity assay, the active fractions are combined and the pool is concentrated where appropriate by ultrafiltration (30 000 MWCO). A protein determination and a quantitative activity assay follow (see Example 9).

TABLE 2

Purification of the sPQQGDH from *E. coli* DH5α::pAI3-KOZ65

| | Vol. [ml] | Total protein [mg] | Total activity [U] | Specific activity [U/mg] | Yield [%] |
|---|---|---|---|---|---|
| Sample loaded onto column | 11.2 | 103.6 | 15 680 | 151 | 100 |
| Active fractions | 4.45 | 13.50 | 15 085.5 | 1117 | 96 |

Only one active band was detected in an SDS gel and in a native gel. The protein was thus pure. Based on the original culture, 48.2 mg of pure protein were obtained per 1 of culture.

Example 7

Preparation of Recombinant sPQQGDH From W3110 Strains and Testing of the Thermal Stability For comparison of the thermal stability of recombinant sPQQGDH from LMD79.41 (plasmid pAI3-wt) and the sPQQGDH from KOZ65 (plasmid pAI3-KOZ65), the strains W3110::pAI3-wt and W3110::pAI3-KOZ65 were cultured in 200 ml of TB medium with 100 μg/ml ampicillin. After the cultures had reached an $OD_{600}$ of 3, the bacteria were centrifuged at 4600 rpm for 10', and the pellets were taken up in each case in 25 ml of fresh TB medium with 100 μg/ml ampicillin. AHT was added to a concentration of 2 μg/ml for induction, and the cells were shaken at 22° C. for 6 h. The cells were then pelleted anew, and the pellets were stored at −80° C. until processed further. The frozen cells were resuspended in each case in 25 ml of MOPS buffer (10 mM MOPS pH 8, 2.5 mM $CaCl_2$, 0.05% Triton X-100) and disrupted by ultrasound treatment until the suspension became distinctly clearer. Cell residues were removed at 20 000 rpm and 4° C. for 30 min, and the supernatant was purified on a Toyopearl CM-650 M column (20 ml bed volume). For this purpose, after the sample loading the column was washed with 50 ml of MOPS buffer (see above) and then bound protein was eluted with a gradient from 0 to 0.6 mM NaCl in MOPS buffer. Fractions with GDH activity were pooled, and the activity of the pool was determined (see Example 9).

The thermal stability of both enzyme preparations was determined by dilution with 50 mM Pipes, pH 6.5 with 1 mM $CaCl_2$, 0.1% Triton X-100, 0.1% BSA and 5 μM PQQ to adjust to a solution of 20 U/ml. Aliquots of this solution were incubated in parallel at 4° C., 50° C., 57° C. and 64° C. for 60 min. The remaining activity is then found, based on the value at 4° C. as 100%, as follows (as triplicates; see Example 9):

| Strain | 50° C. | 57° C. | 64° C. |
|---|---|---|---|
| W3110::pAI3-wt | 95.1 ± 2.9 | 20.7 ± 0.8 | 3.4 ± 0.0 |
| W3110::pAI3-KOZ65 | 95.1 ± 1.6 | 56.8 ± 3.6 | 8.7 ± 0.3 |

Example 8

Preparation by High Cell-Density Fermentation

The fermentation was carried out in a 10 litre steel fermenter (BIOSTAT C) from Braun.

5 litres of (modified) Riesenberg medium were employed for this purpose

| | |
|---|---|
| $KH_2PO_4$ | 13.3 g |
| $(NH4)_2HPO_4$ | 4.0 g |
| Citric acid | 1.7 g |
| Magnesium sulphate × $7H_2O$ | 1.2 g |
| Thiamine | 0.5 g |
| Tryptone | 1.2 g |
| Yeast extract | 2.4 g |
| Trace element solution | 50 ml |
| Dist. water | ad 880 ml |
| Glucose | 5 g in 100 ml of dist. water (sterilized separately) |
| Ampicillin | 100 mg (separately dissolved in 20 ml of dist. water and sterilized by filtration) |
| Trace element solution | |
| Titriplex III | 0.84 g |
| Fe(III) citrate | 6.00 g |
| $MnCl2 × 4H_2O$ | 1.50 g |
| $ZnCl2 × 2H_2O$ | 0.80 g |
| $H_3BO_3$ | 0.30 g |
| $Na_2MoO_4 × 2H_2O$ | 0.25 g |
| $CoCl_2 × 6H_2O$ | 0.25 g |
| $CuCl_2 × 2H_2O$ | 0.15 g |
| Dist. water | ad 1000 ml |

The pH was adjusted after addition of all the medium ingredients to 6.80 with 5 N NaOH.

The nutrient solution was inoculated with 100 ml of a preculture (LB medium with 100 mg/l ampicillin) grown at 37° C. overnight.

The OD after the inoculation was 0.066. The aeration rate was adjusted to 2 l/min, the stirrer speed to 500 rpm and the temperature to 37° C. The pH was adjusted to pH 7.25 with 5 N $NH_3$ and kept constant throughout the fermentation.

After growth for 12 hours, the $pO_2$ had fallen below 10% and most of the glucose had been consumed. After growth for 15 hours, the $OD_{600}$ was 14.2 and the dry matter was 6.2 g/l. Feeding was started at this time. The feed solution consisted of:

| | |
|---|---|
| Glucose | 700 g |
| Magnesium sulphate × $7H_2O$ | 28 g |
| Thiamine | 0.5 g |
| Tryptone | 1.2 g |
| Yeast extract | 2.4 g |
| Dist. water | ad 1000 ml |

The solution was sterilized by filtration. It was fed to the fermenter by a tubing pump. The pump delivery was controlled via the target $pO_2$, which was set at 20%. Control took place in such a way that the pump is switched on at a $pO_2$ of >20%, and new glucose is fed in. The oxygen consumption which starts up then causes the $pO_2$ to fall again. The pump is switched off if the $pO_2$ falls below 20%. The stirrer speed and aeration rate were not changed. The $OD_{600}$ after growth for 64 hours was 50.2. 5 litres of double concentrated TB medium were then fed into the fermenter, the temperature was reduced to 22° C., and the aeration rate was set at 4 l/min.

The stirrer speed was raised to 700 rpm. The culture was then induced with 10 ml of anhydrotetracycline solution (2 mg/ml in DMF) for 6 hours. A sample was then taken to determine the activity. The activity assay revealed a value of 223 U/ml of culture liquid. Over 220 mg of pure enzyme were obtained per ml of culture.

Example 9

Procedure for the Activity Assay

The measurements were carried out in an "Ultraspec 2000" photometer. The following solutions are employed for this purpose:
PIPES: 50 mM pH 6.5 incl. 2.2% Triton X-100
Glucose: 1 M in $H_2O$
PMS: 3 mM phenazine methosulphate in $H_2O$
NTB: 6.6 mM nitrotetrazolium blue in $H_2O$
$CaCl_2$: 1 M in $H_2O$
PQQ: 3 mM in DMSO
EDB *: 50 mM PIPES pH 6.5 incl. 0.1% Triton X-100, 1 mM $CaCl_2$, 0.1% BSA, 6 µM PQQ.

EDB=enzyme dilution buffer
The working reagent consists of the following components:
25.5 ml of PIPES incl. 2.2% Triton X-100
0.9 ml of Glucose
2.0 ml of PMS
1.0 ml of NTB
The EDB and the working reagent should if possible be made up freshly.
Procedure for the activity determination:
Introduce 20 µl of the chosen sample dilution into microcuvettes (20 µl of EDB instead of the sample solution are added as zero value),
add 600 µl of working reagent and immediately start the measurement at 570 nm for 3 minutes.
Calculation of the activity:
The change in absorption is measured as change in extinction/min; one unit of GDH generates 0.5 µmol of formazan per minute. The following formula applies:

$U$/ml=change in extinction/min×1.54×dilution factor
$\epsilon=40200 M^{-1} cm^{-1}$

---

The invention claimed is:

1. A soluble pyrroloquinoline quinone glucose dehydrogenase (sPQQGDH) having the amino acid sequence of wild-type *Acinetobacter* LMD 79:41 (numbering as shown in SEQ ID NO: 2), wherein compared to the amino acid sequence of wild-type *Acinetobacter* LMD 79:41 (numbering as shown in SEQ ID NO: 2):
   a) the following amino acids are exchanged:
      i) position 21 has a N;
      ii) position 41 has an S;
      iii) position 47 has an L;
      iv) position 121 has a V or an A;
      v) position 149 has an A;
      vi) position 213 has an S;
      vii) position 244 has an I;
      viii) position 320 has a G;
      ix) position 391 has an S;
      x) position 452 has an S;
      xi) position 474 has an R; and
      xii) position 480 has a Q; and
   b) optionally at least one of the following amino acids are also exchanged:
      i) position 16 has an H;
      ii) position 18 has an L;
      iii) position 20 has an F;
      iv) position 40 has a G;
      v) position 48 has an I;
      vi) position 61 has an A;
      vii) position 111 has a T;
      viii) position 154 has a D;
      ix) position 190 has a D;
      x) position 293 has an A;
      xi) position 311 has an S;
      xii) position 314 has an A;
      xiii) position 324 has an L;
      xiv) position 333 has an M;
      xv) position 339 has an S;
      xvi) position 355 has a G;
      xvii) position 366 has a D;
      xviii) position 417 has an N; or
      xix) position 418 has an A.

2. sPQQGDH of claim 1, wherein compared to wild-type *Acinetobacter* LMD 79:41 (numbering as shown in SEQ ID NO: 2) at least one of the following amino acids are also exchanged:
   i) position 16 has an H;
   ii) position 18 has an L;
   iii) position 20 has an F;
   iv) position 40 has a G;
   v) position 48 has an I;
   vi) position 61 has an A;
   vii) position 111 has a T;
   viii) position 154 has a D;
   ix) position 190 has a D;
   x) position 293 has an A;
   xi) position 311 has an S;
   xii) position 314 has an A;
   xiii) position 324 has an A;
   xiv) position 333 has an M;
   xv) position 339 has an S;
   xvi) position 366 has a D;
   xviii) position 417 has an N; or
   xix) position 418 has an A.

3. sPQQGDH of SEQ ID NO. 12.

4. Process for preparing the sPQQGDH according to claim 1, which comprises cultivating a microorganism which expresses the sPQQGDH, and then isolating the sPQQGDH.

5. Process for preparing the sPQQGDH according to claim 2, which comprises cultivating a microorganism which expresses the sPQQGDH, and then isolating the sPQQGDH.

6. Process for preparing the sPQQGDH according to claim 3, which comprises cultivating a microorganism which expresses the sPQQGDH, and then isolating the sPQQGDH.

7. Reagent for detection of glucose comprising one or more sPQQGDH enzymes according to claim 1.

8. Reagent for detection of glucose comprising one or more sPQQGDH enzymes according to claim 2.

9. Reagent for detection of glucose comprising the sPQQGDH enzyme according to claim 3.

* * * * *